United States Patent
Holmes et al.

(10) Patent No.: US 8,945,070 B2
(45) Date of Patent: Feb. 3, 2015

(54) VETERINARY SYRINGE FOR MULTIPLE INJECTIONS

(75) Inventors: Robert William Lachlan Holmes, Auckland (NZ); Rodney Gordon Walker, Hamilton (NZ); Todd Donald Ebbett, Hamilton (NZ); Colin Anthony Standing, Hamilton (NZ); Peter Robert Williams, London (GB); Giovanni Ciampa, Gladesville Sydney (AU); Michael Rossignuolo, Melbourne (AU); Robert John Smith, Sydney (AU)

(73) Assignee: Merial Limited, Duluth, GA (US)

( * ) Notice: Subject to any disclaimer, the term of this patent is extended or adjusted under 35 U.S.C. 154(b) by 1032 days.

(21) Appl. No.: 12/921,807

(22) PCT Filed: Mar. 11, 2009

(86) PCT No.: PCT/NZ2009/000035
§ 371 (c)(1),
(2), (4) Date: Mar. 10, 2011

(87) PCT Pub. No.: WO2009/113883
PCT Pub. Date: Sep. 17, 2009

(65) Prior Publication Data
US 2011/0160674 A1    Jun. 30, 2011

(30) Foreign Application Priority Data

Mar. 14, 2008   (NZ) ........................ 566713

(51) Int. Cl.
*A61M 5/00* (2006.01)
*A61M 5/24* (2006.01)
*A61M 5/315* (2006.01)

(52) U.S. Cl.
CPC ............... *A61M 5/24* (2013.01); *A61M 5/2425* (2013.01); *A61M 5/2459* (2013.01); *A61M 5/31511* (2013.01); *A61M 2005/005* (2013.01); *A61M 2005/2414* (2013.01); *A61M 2005/31516* (2013.01)
USPC ........................................................ 604/232

(58) Field of Classification Search
USPC .............. 604/212–235, 181, 187; 222/94, 97, 222/144, 167
See application file for complete search history.

(56) References Cited

U.S. PATENT DOCUMENTS

2006/0237477 A1* 10/2006 Gregg .............................. 222/94
2008/0058732 A1* 3/2008 Harris ........................... 604/235

* cited by examiner

*Primary Examiner* — Aarti B Berdichevsky
*Assistant Examiner* — Bradley Osinski
(74) *Attorney, Agent, or Firm* — Judy Jarecki-Black; Chad Kitchen; Merial Limited

(57) ABSTRACT

A trigger operated syringe (100) for intramammary injection of antibiotics has a fluid containing syringe cartridge (203) activated by a plunger (206) which is inserted into the syringe cartridge (203A) and expels fluid when the trigger (205) is pulled. A syringe cartridge holding mechanism (223) holds the syringe cartridge in place until the trigger (205) is released and the plunger (206) retracted. Single syringe cartridge (203) and multiple syringe cartridge (204) versions are disclosed. The plunger moves in a direction which is effectively perpendicular to the direction of movement of the trigger, allowing for ease of injection to a cow's teats, and ejection of the spent cartridges.

12 Claims, 28 Drawing Sheets

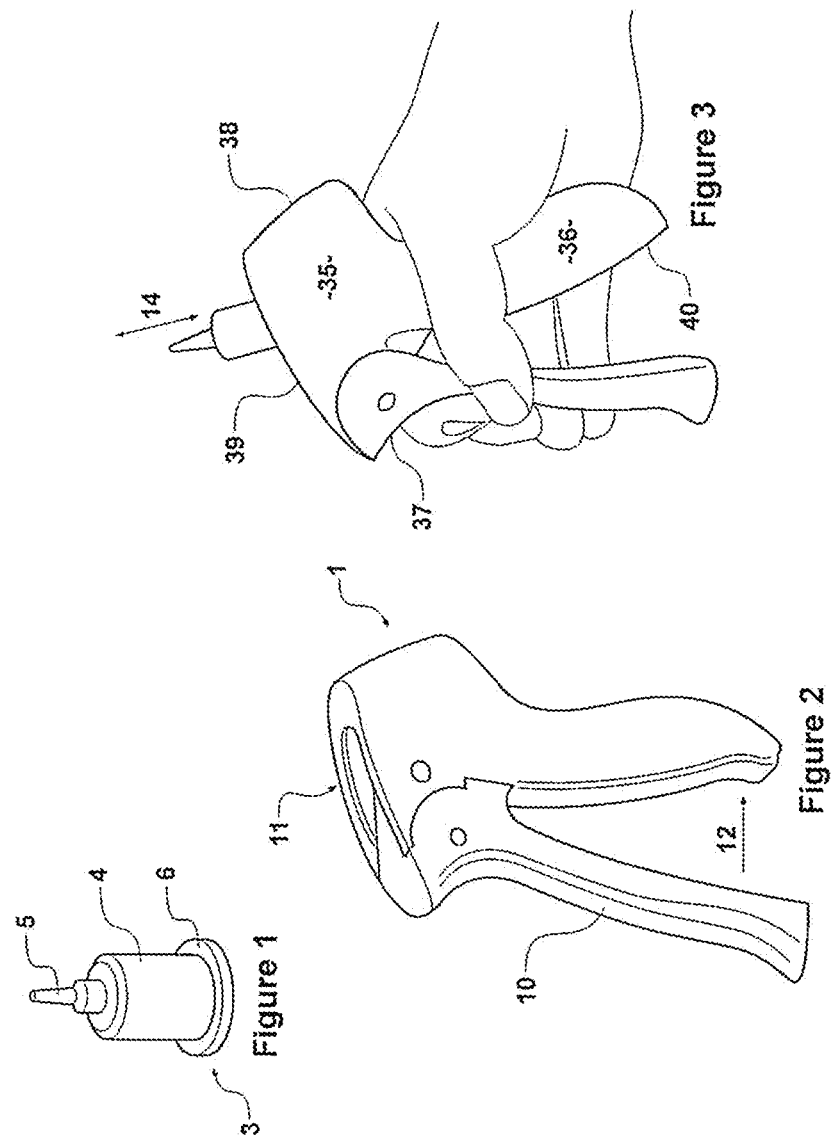

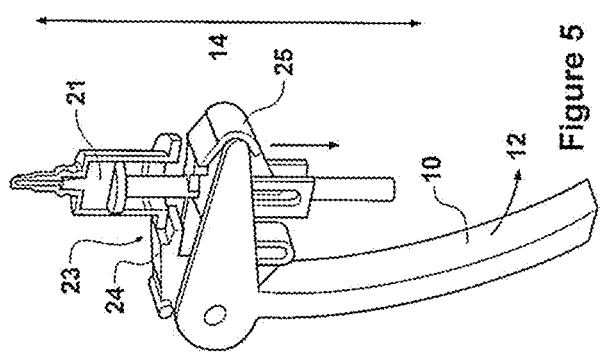
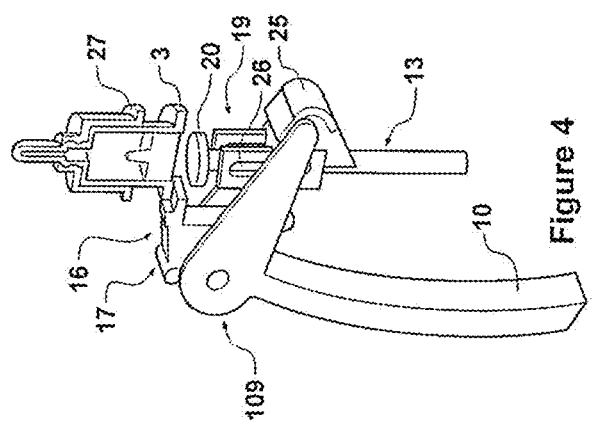

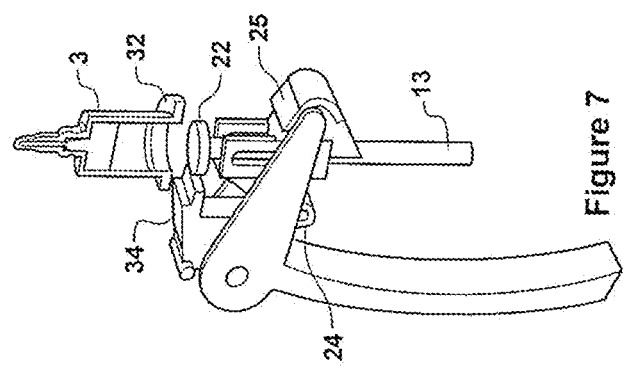
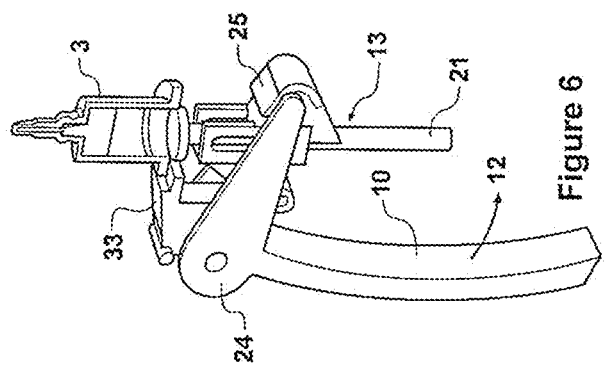

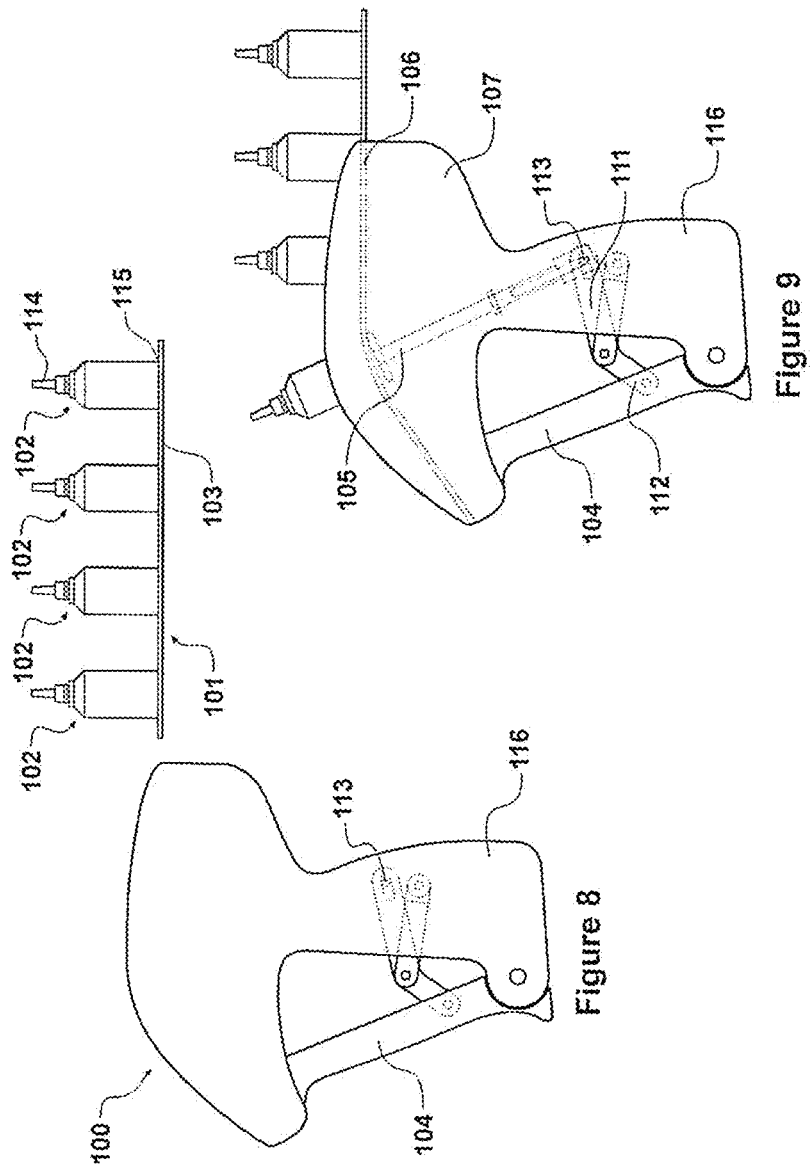

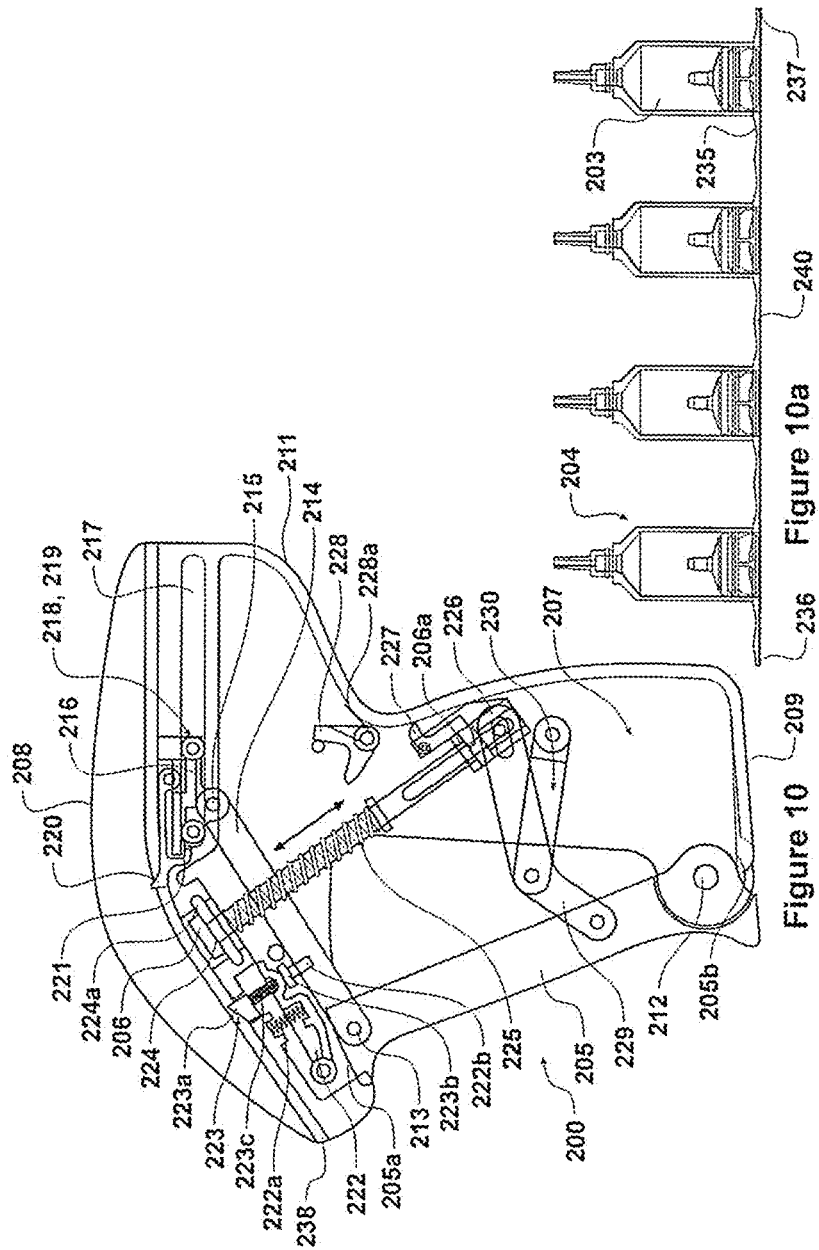

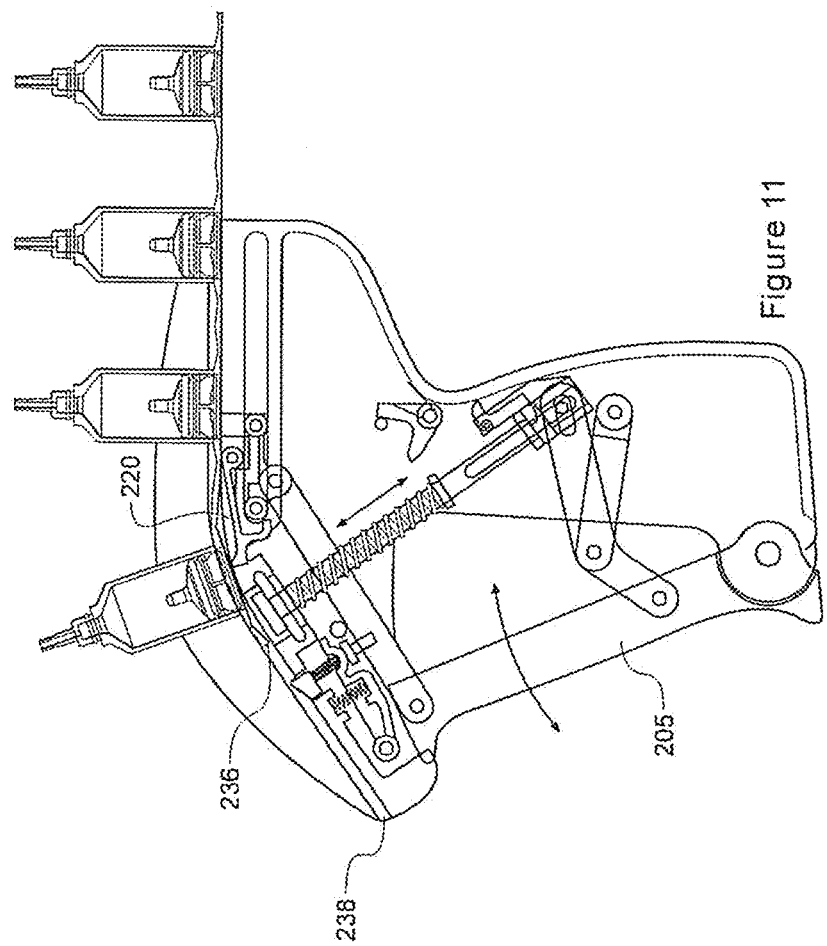

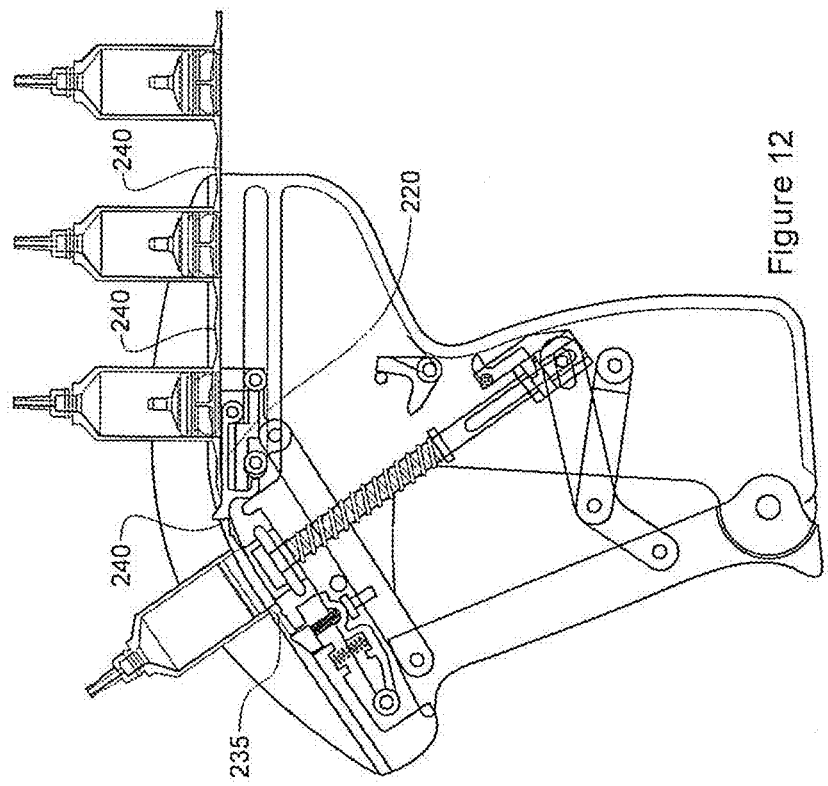

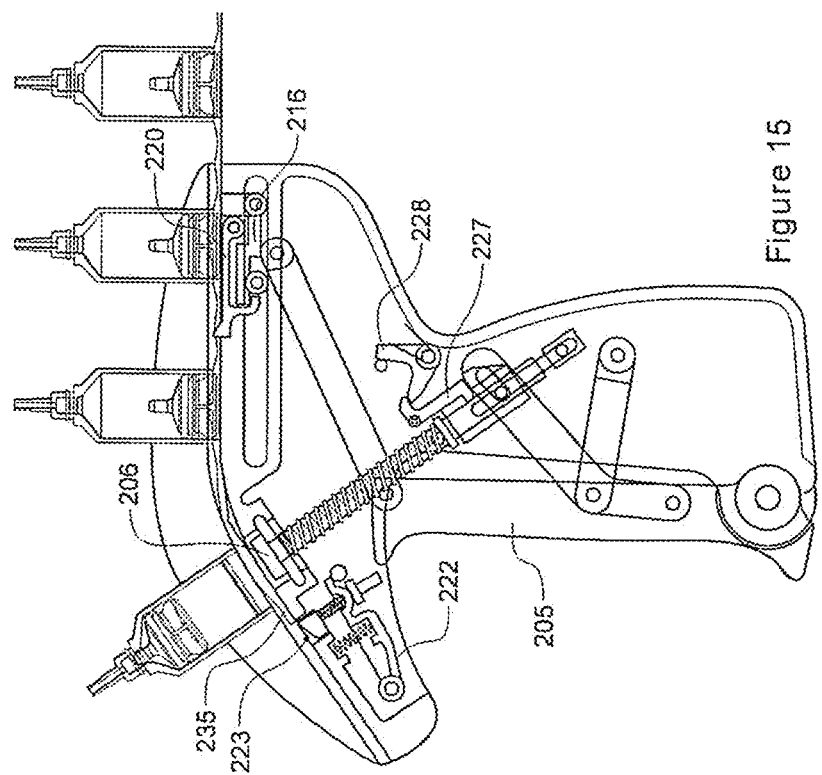

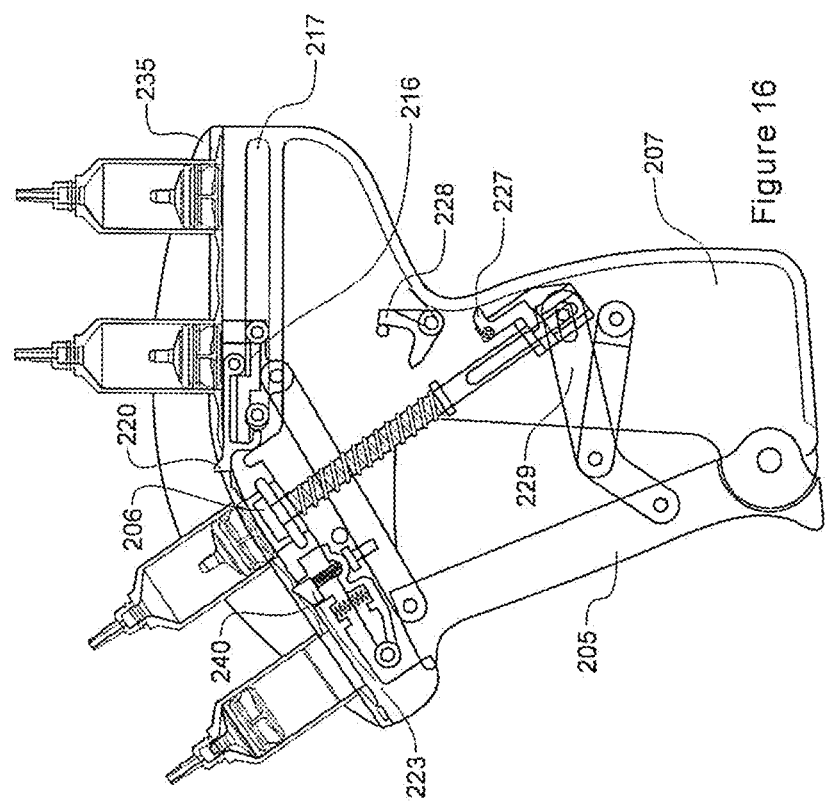

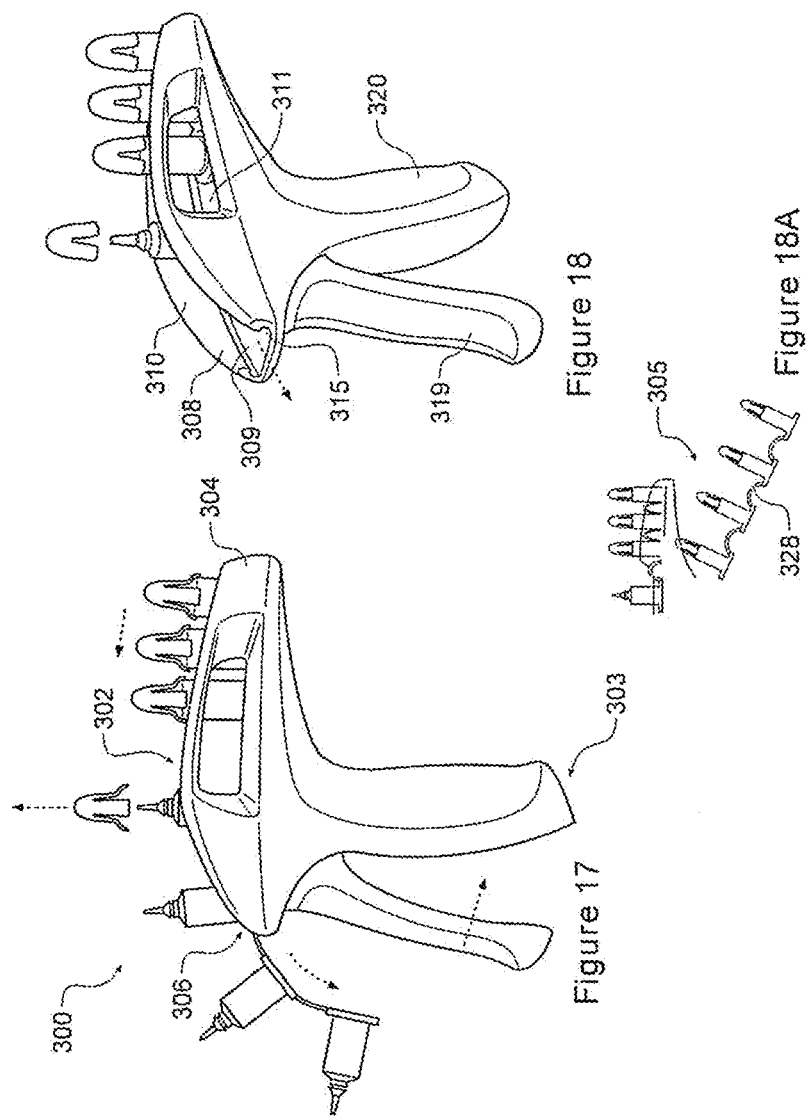

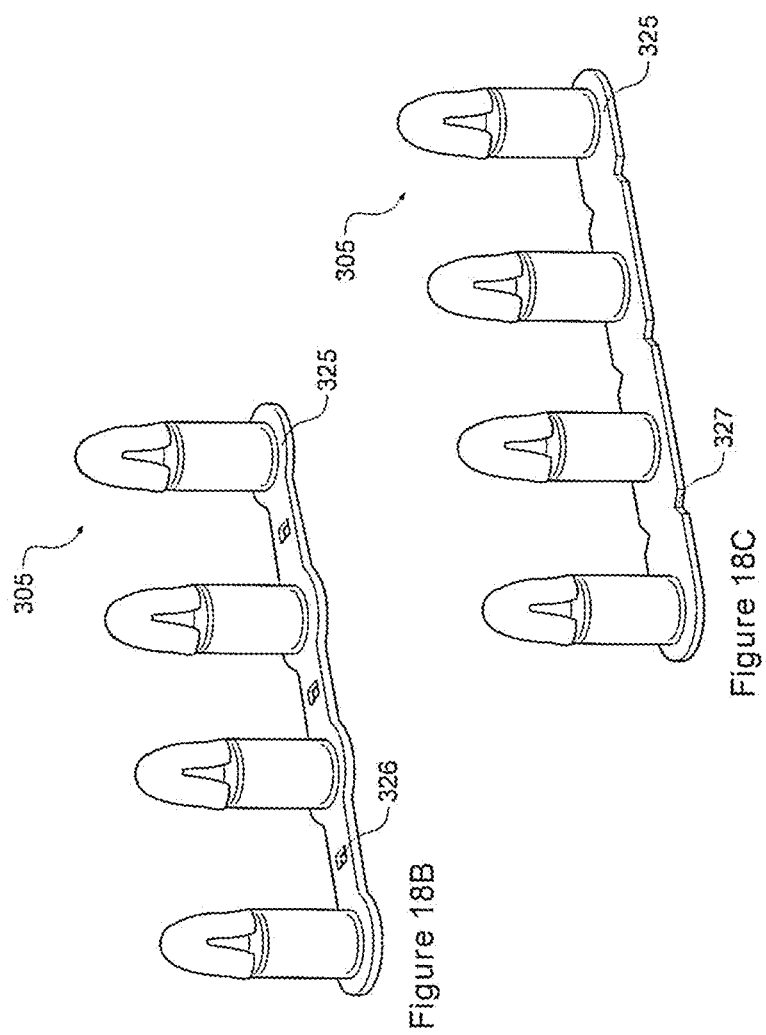

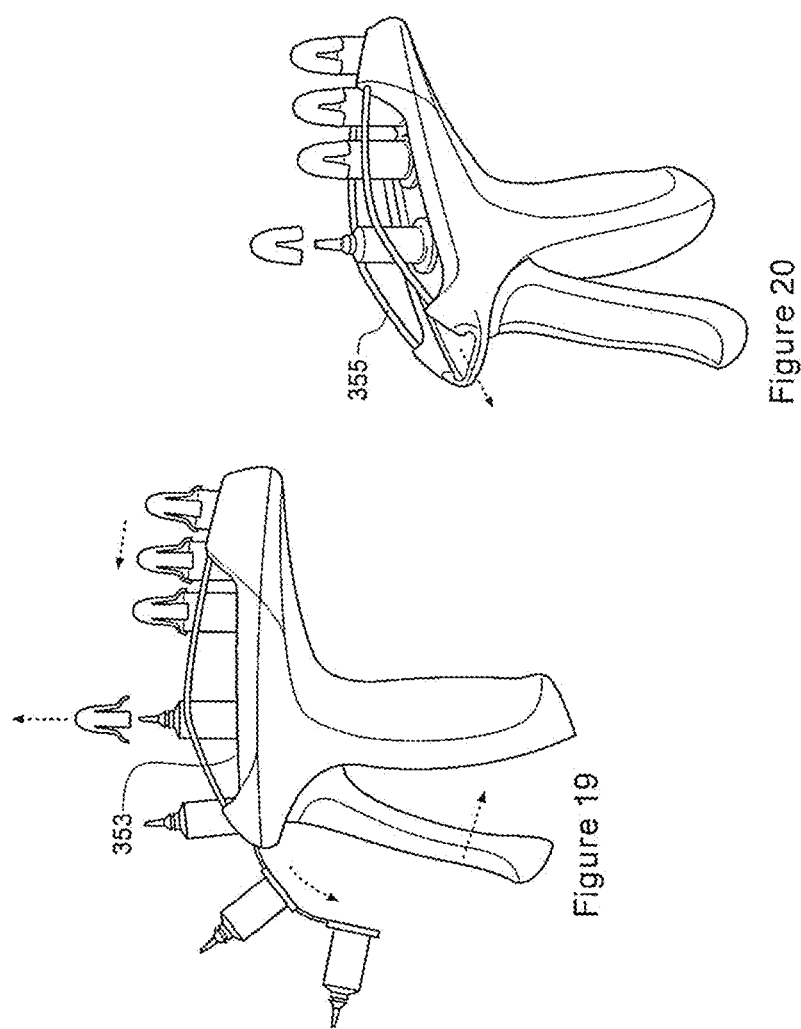

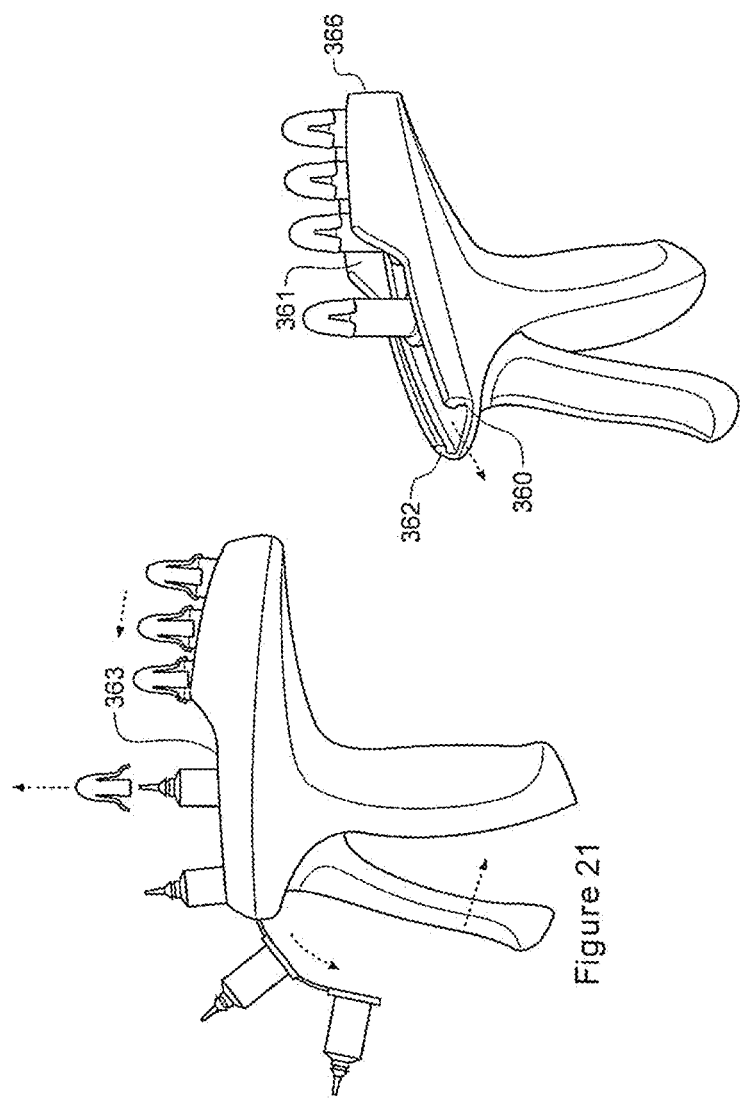

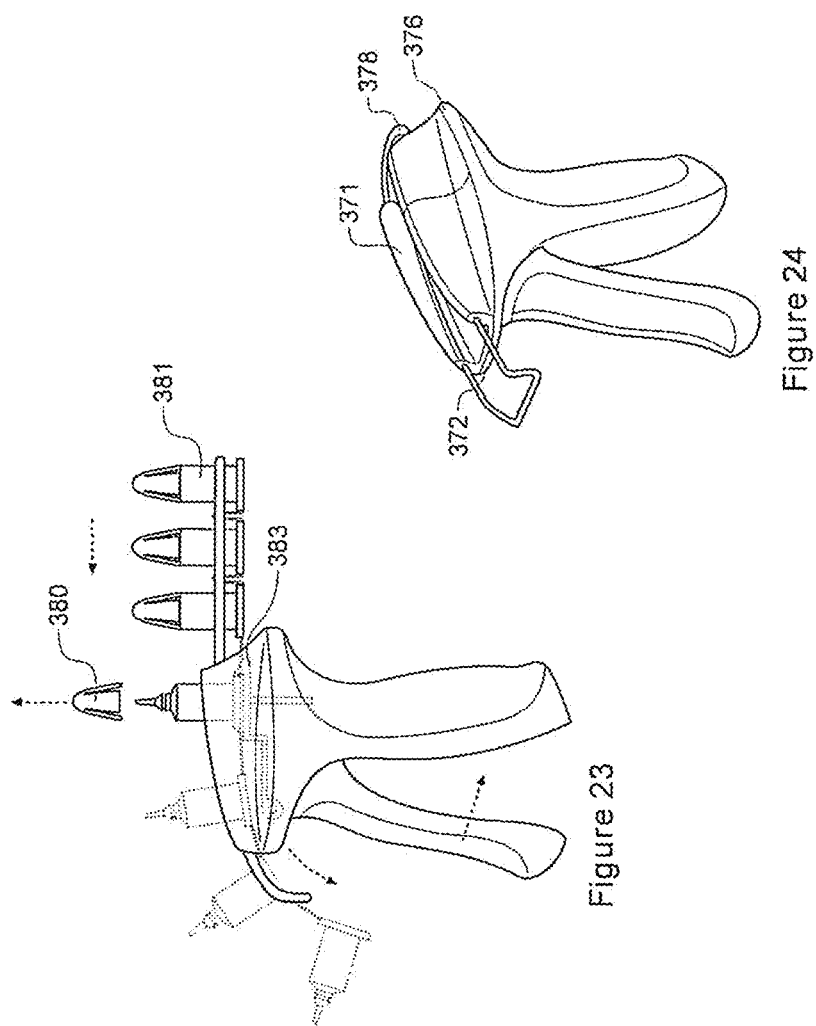

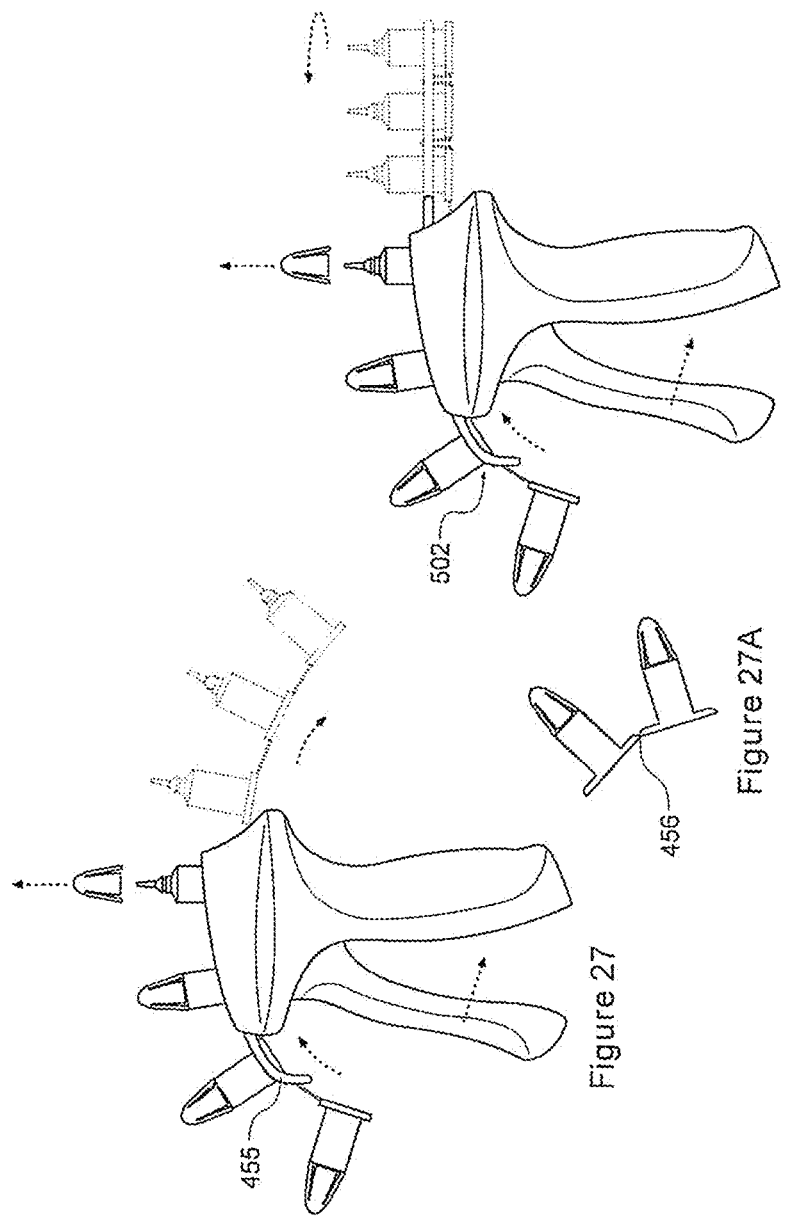

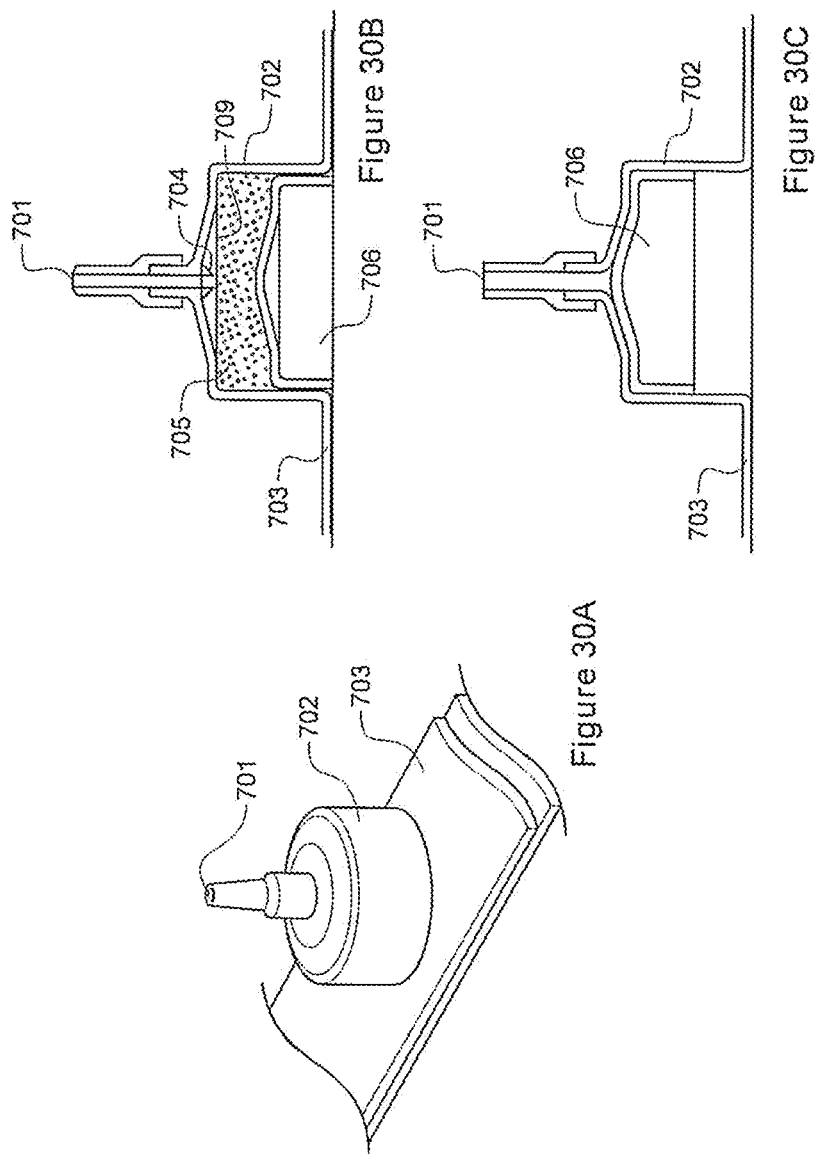

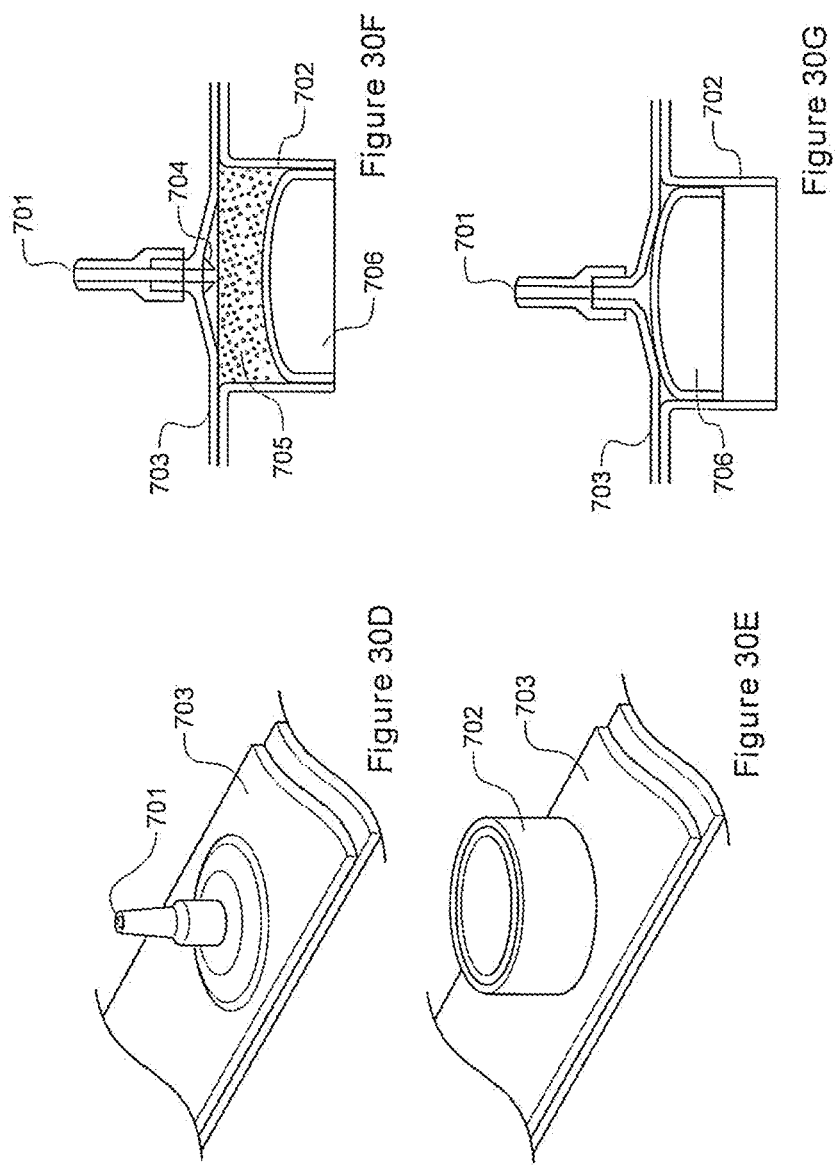

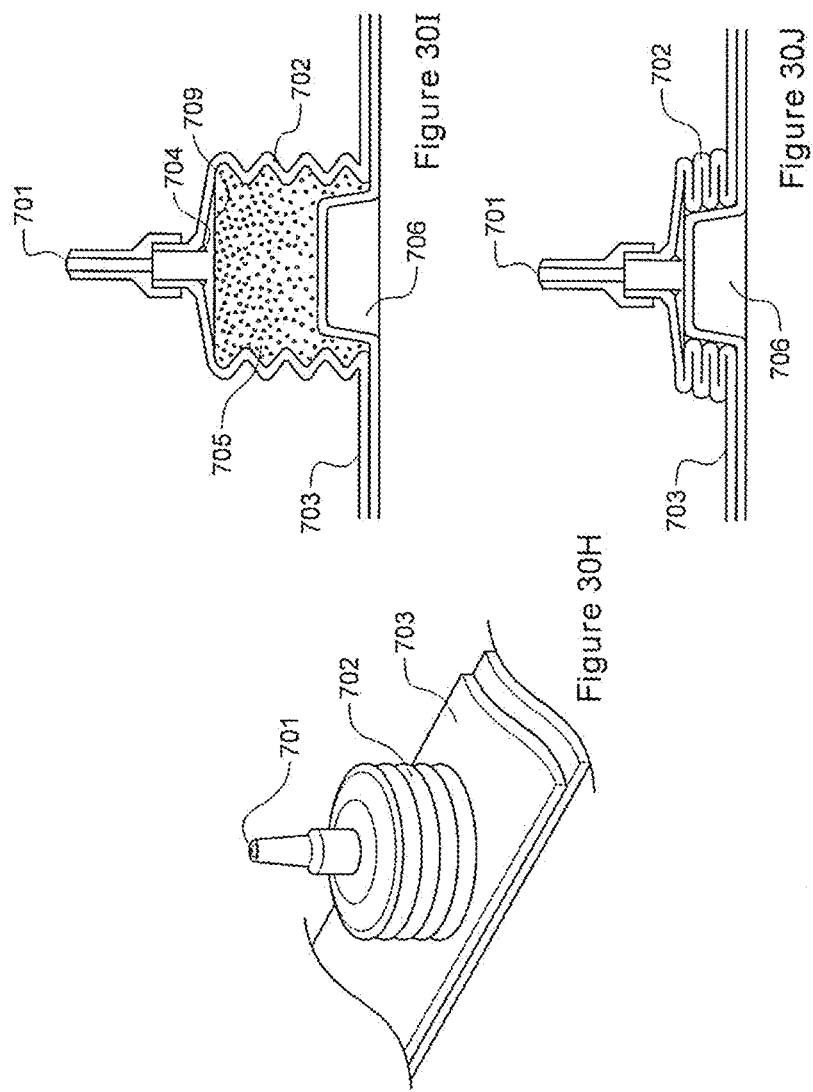

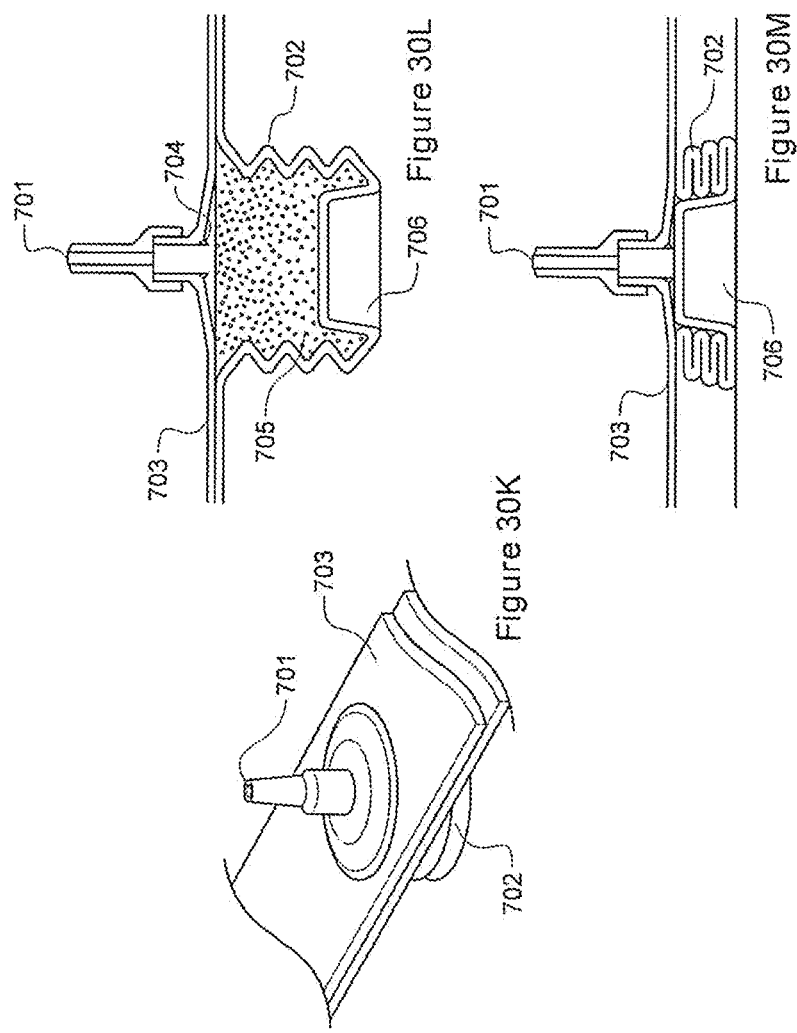

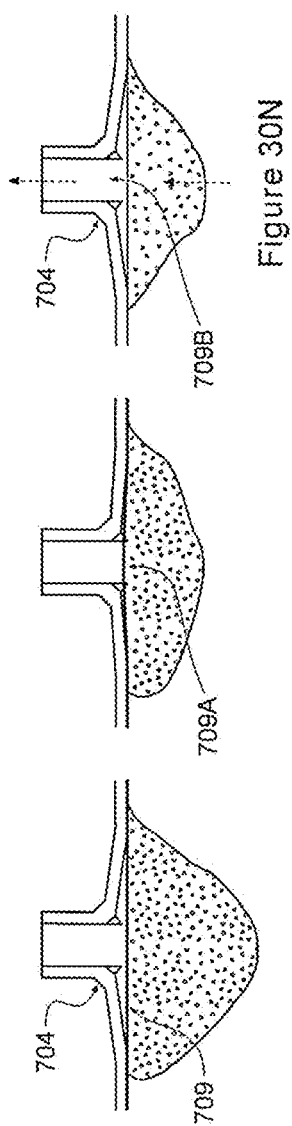

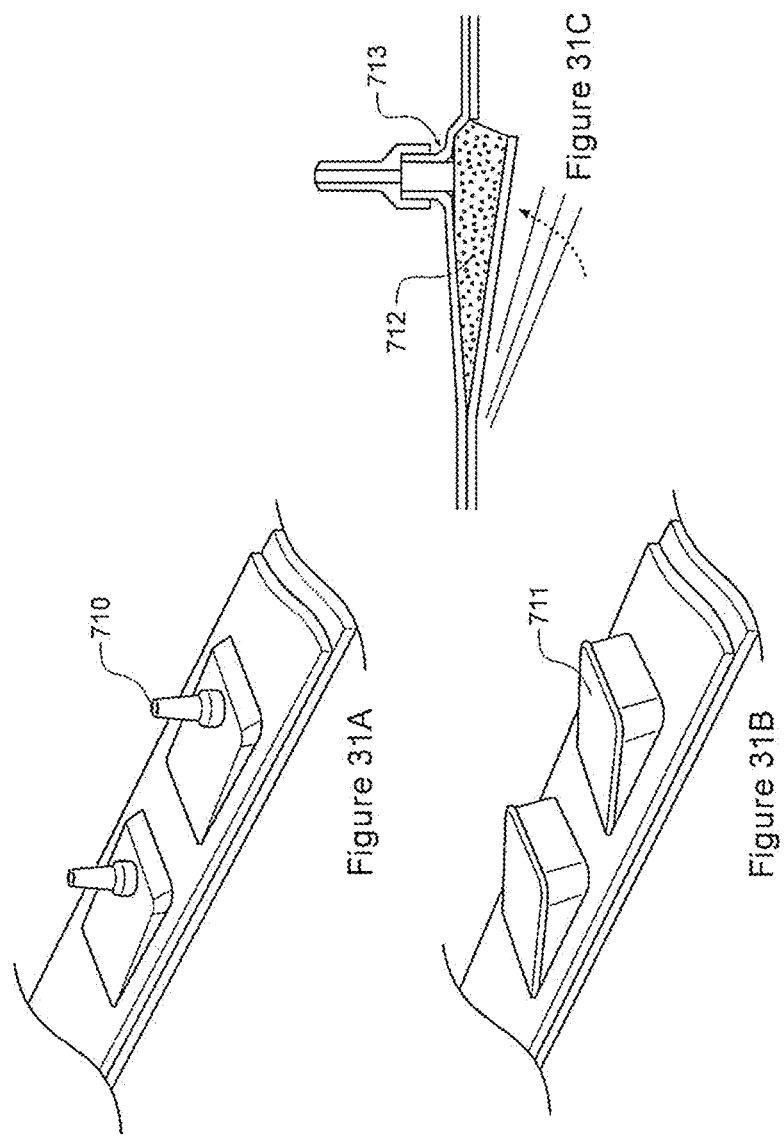

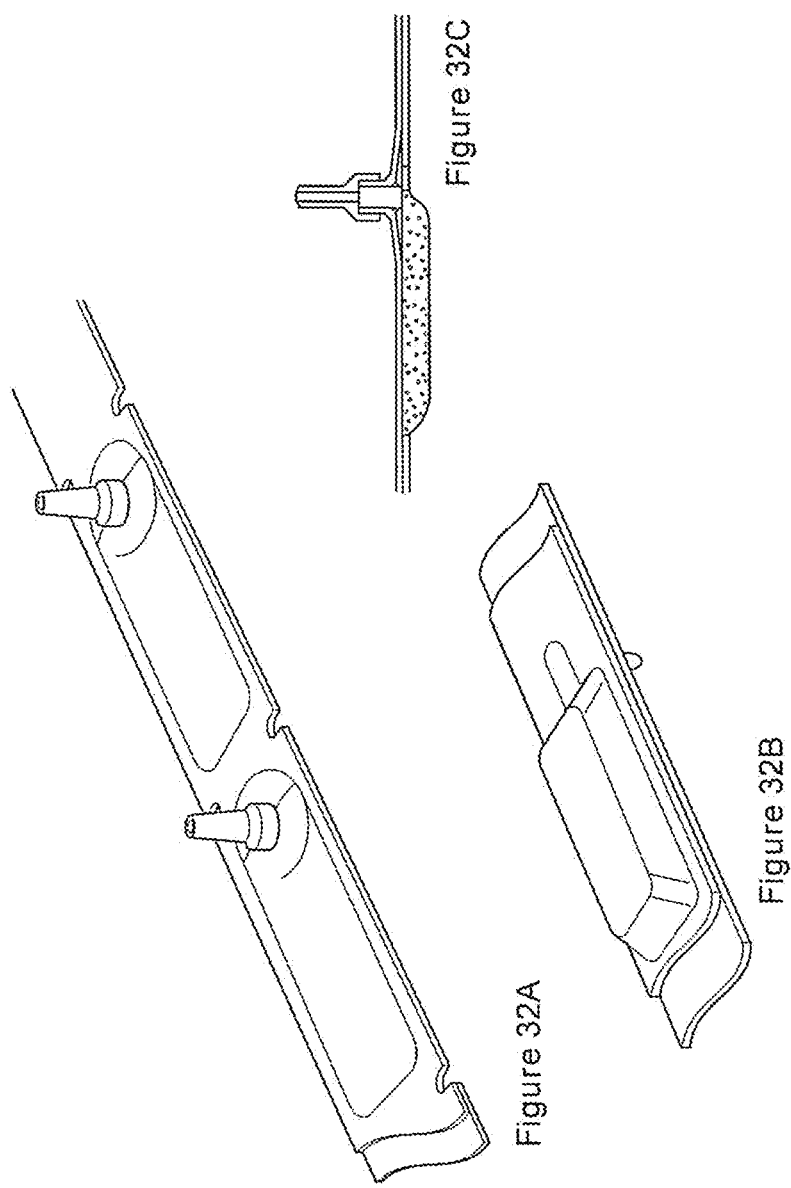

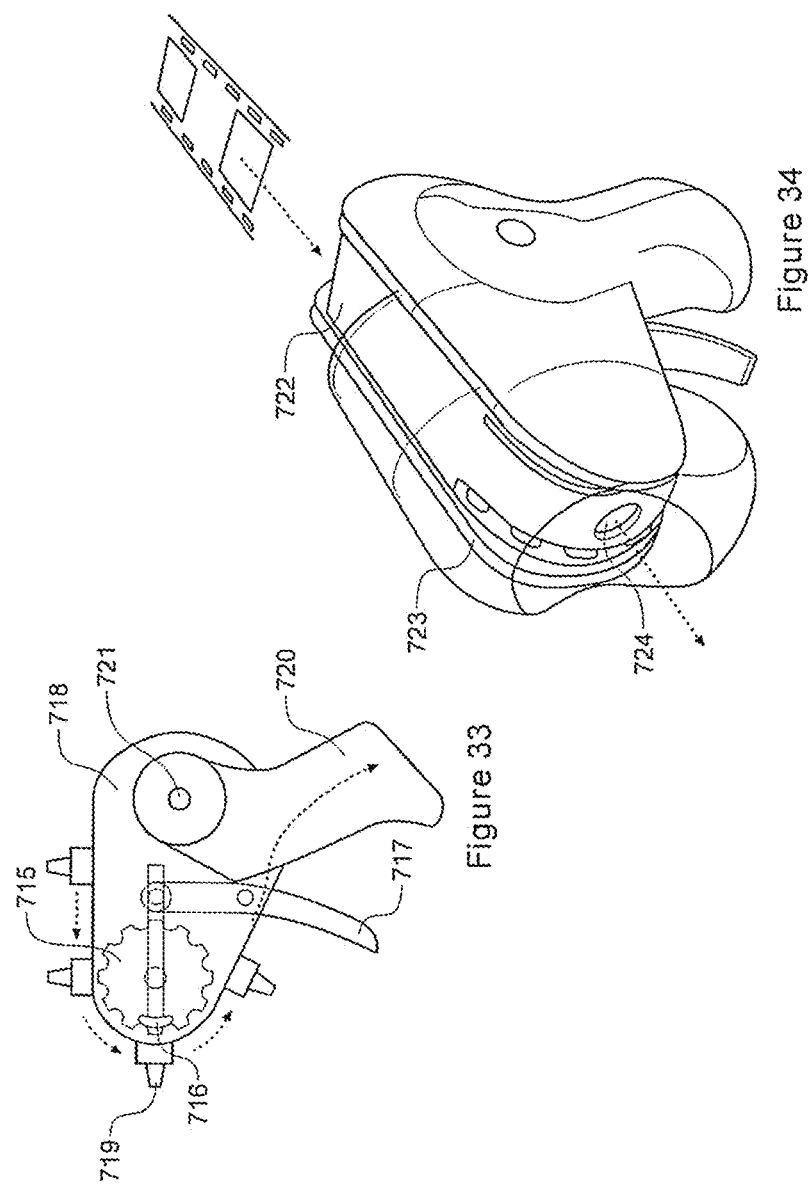

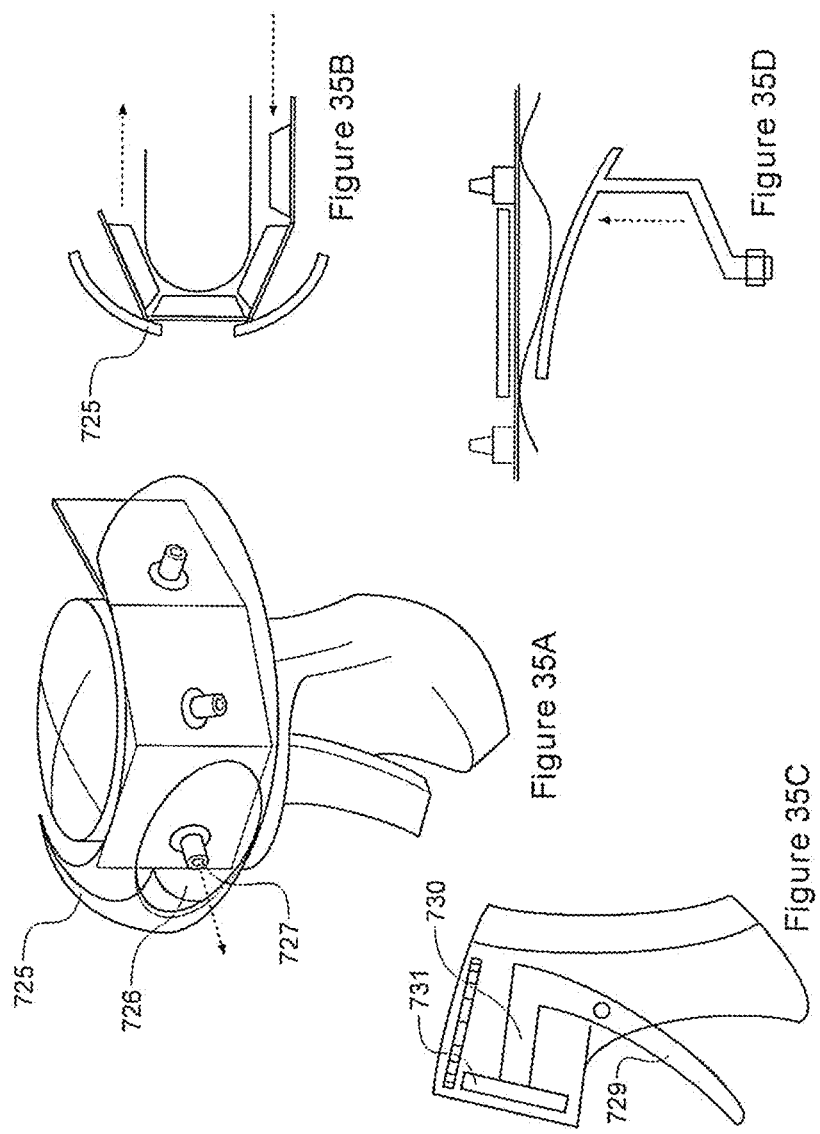

VETERINARY SYRINGE FOR MULTIPLE INJECTIONS

FIELD OF THE INVENTION

The invention relates to veterinary syringes for multiple injections, i.e. syringes for use in injecting animals especially where many animals have to be injected as is the case in the treatment of a large flock or herd of farmed animals.

BACKGROUND OF THE INVENTION

U.S. Pat. No. 4,020,838 describes an animal dosing syringe (for drenching via a nozzle to the throat or by needle for injection). It is in the shape of a gun having a handle at right angles to the nozzle.

U.S. Pat. No. 6,554,161 describes a multi-barrel dispensing apparatus. The interchangeable components allow change in dosages supplied.

U.S. Pat. No. 5,199,949 describes a multiple pharmaceutical syringe. It has a number of sterile cartridges containing insulin held within its housing. The cartridges are pierced and fluid flows into an accumulator form which it can be dispensed via a needle assembly.

U.S. Pat. No. 5,122,057 describes means for dosing dental cartridges—the cartridges are placed in a breech opening and held in place in a syringe gun before the paste is expelled by the operation of a piston operated by a lever or screw action.

U.S. Pat. No. 6,616,634 shows an ergonomic syringe designed to reduce fatigue and strain in surgical procedures.

US patent application 2008/0058732 describes a hypodermic syringe and a plurality of single use cartridges able to be successively loaded into the syringe for providing rapid dispensing of a medicament to numerous human patients without contamination. It is in the shape of a gun having a trigger at right angles to the cartridge dispenser.

U.S. Pat. No. 5,022,563 describes a dispenser-gun assembly and dispenser which are operative for dispensing viscous fluids without significant amounts of post extrusion. It is in the shape of a gun having a handle and trigger at right angles to the dispensing nozzle.

U.S. Pat. No. 5,692,642 describes a dispenser adapter apparatus particularly for use in the dental profession, which allows dispensing of multiple types of materials with use of a single dispensing device. It is in the shape of a gun having a trigger at right angles to the dispensing nozzle.

U.S. Pat. No. 5,964,736 describes a closed delivery system for the handling of injectable biological products and vaccines used in the treatment and prevention of livestock diseases. The system embodies a multidose prefilled disposable cartridge and a metered pistol grip syringe body.

U.S. Pat. No. 4,738,664 relates to a pistol grip syringe apparatus which has a removable container for the fluid to be dispensed from the syringe and a piston which disconnects from a driving rod of the apparatus with the container.

Australian patent 652664 relates to a gun for dispensing discrete doses of a fluid product from a cartridge associated with the gun. The trigger is at right angles to the dispensing cartridge.

It is a common practice for entire dairy herds to be treated with intramammary antibiotics at "drying-off". Currently, antibiotics are administered via very basic disposable syringes. Each quarter of a cow's udder is treated, so for a herd of 250 cows, this requires 1,000 doses. A common complaint is that existing syringes are awkward to hold, hard to squeeze, and hard on the user's fingers, particularly when used repeatedly during application of more than a few treatments.

With traditional syringes, only two fingers and either the thumb or palm can be used to exert force to administer the contents of the cartridge. Further still, the longitudinal axis of the syringe is aligned parallel with the axis of force applied by the user. Thus, to inject an udder located on the underside of the cow, the administrator must awkwardly contort their body to try to get the syringe needle facing upward, which has proven awkward and exhausting.

Another problem with traditional syringes is the need to inject several teats in a similar position. At present this requires constant manual changing of used syringes, reloading and repositioning of the user to recommence syringing. It is also difficult to know when the whole of the contents of a cartridge have been dispensed.

Visibility of the syringe nozzle during dispensing is also important during intramammary application, for visual guidance. Due to the problems mentioned above it can be very difficult to see the syringe nozzle and guide it to the correct position during application. Another problem is the space confinements under a cow's udder. Some udders hang very low to the ground and teats might also be very close to the animal's leg. Traditional syringes are not very compact and their bulkiness in conjunction with the limited space makes it difficult to successfully manoeuvre the syringe onto any given teat.

A further important aspect of intramammary application is sterility. The syringe must be kept sterile to prevent contamination to teats and cross contamination between the teats of one cow and the teats of other cows, in order to minimise the risk of infection. The design of existing syringes does not make it easy to maintain a sterile environment during intramammary application.

The prior art listed above describes various forms of dispensing devices which are all in the shape of guns having a handle and/or trigger at right angles to the dispensing nozzle of the device. In each of these prior art devices, the longitudinal axis of the syringe cartridge is aligned parallel with the axis of force applied by the user to dispense the contents of the syringe. Although such devices may be suitable for use with human patients who are generally cooperative, and at injection or administration sites which are unencumbered and easy to access, they are not very suitable for administering to areas such as the udder of an animal such as a cow, which is low to the ground and in a confined space, and therefore difficult to access. The administrator must awkwardly contort their body to try to get the dispensing nozzle of the gun facing upward, which is uncomfortable and exhausting, especially as the gun may be bulky and it may be difficult to see and guide the nozzle of the gun to the correct position. Furthermore the animals may be moving or uncooperative, making administration even more difficult.

Accordingly, there exists a need for an improved device that is easier to use, less exhausting, reliable, compact, inexpensive to manufacture, and/or which minimises the risk of contamination occurring during applications.

In this specification unless the contrary is expressly stated, where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

SUMMARY OF THE INVENTION

It is an object of the invention to provide an improved syringe that ameliorates some of the disadvantages and limitations described above or that at least provides the public with a useful choice.

In one aspect the invention provides a syringe cartridge applicator for dispensing a fluid from a syringe cartridge, the syringe cartridge applicator comprising:

an applicator trigger moveable from an extended position to a retracted position;

a plunger assembly interfaced with the applicator trigger, wherein movement of the applicator trigger from the extended position to the retracted position results in the plunger assembly driving the fluid from the syringe cartridge; and a syringe cartridge holding assembly, the syringe cartridge holding assembly adapted to removably receive a syringe cartridge, and to hold the syringe cartridge in a dispensing position such that a longitudinal axis of the syringe cartridge is inclined at a predetermined angle relative to a direction in which the applicator trigger is moved when moved between the extended position and the retracted position.

Preferably, the predetermined angle is greater than about 45 degrees and less than about 135 degrees. Alternatively, the predetermined angle is greater than about 60 degrees and less than about 120 degrees.

Preferably, when a syringe cartridge is in the dispensing position, the longitudinal axis of the syringe cartridge is oriented substantially perpendicular to the direction in which the applicator trigger is moved when moved between the extended position and the retracted position.

Preferably, the syringe cartridge applicator includes a guide assembly for slidingly receiving a syringe cartridge in a loading direction oriented substantially parallel to the direction in which the applicator trigger is moved when moved between the extended position and the retracted position.

Preferably the syringe cartridge dispensing device includes a guide assembly for slidingly receiving a syringe cartridge in a loading direction oriented substantially perpendicular to the longitudinal axis of the syringe cartridge.

Preferably the guide assembly includes at least one track for slidingly receiving a portion of a flange of the syringe cartridge.

Preferably wherein the guide assembly includes at least one track for slidingly receiving a cartridge strip made up of a number of individual syringe cartridges supported on a carrier strip.

Preferably the applicator is configured to allow movement of the cartridge strip by the user's thumb to feed one cartridge at a time to the dispensing position.

Preferably the applicator has a syringe cartridge indexing assembly interfaced with the applicator trigger and the syringe cartridge holding assembly, wherein the indexing assembly is adapted to move the next syringe cartridge on the syringe cartridge strip into the dispensing position after the contents of the preceding syringe cartridge have been dispensed such that subsequent movement of the applicator trigger from the extended position to the retracted position results in the plunger assembly driving the fluid from the next syringe cartridge in the syringe cartridge strip.

Preferably, the syringe cartridge holding assembly is adapted such that the cartridge strip follows a curvilinear path as it moves through the syringe cartridge applicator.

Preferably the plunger assembly includes a plunger interfaced with the applicator trigger such that when the applicator trigger is transitioned from the extended position to the retracted position a distal end of the plunger is adapted to enter the syringe cartridge and engage a follower disposed in the syringe cartridge to move the follower within the syringe cartridge to drive the fluid from the syringe cartridge, wherein the distal end of the plunger does not sealingly engage the syringe cartridge.

Alternatively, the plunger assembly includes a plunger interfaced with the applicator trigger such that when the applicator trigger is transitioned from the extended position to the retracted position a distal end of the plunger is adapted to contact a surface of the syringe cartridge to drive the fluid from the syringe cartridge, without entering the syringe cartridge.

Preferably, the syringe cartridge holding assembly includes means which are adapted to remove a protective cap from the syringe cartridge before the contents of the syringe cartridge are dispensed. Preferably, the syringe cartridge holding assembly has a pair of opposing side walls having mechanisms thereon which are adapted to remove the protective cap by contacting one or more protruding shoulders of the protective cap as the syringe cartridge is moved into the dispensing position.

Preferably, the applicator includes a cutting means adapted to remove one or more empty syringe cartridges from the syringe cartridge strip after the fluid has been dispensed therefrom.

In a further aspect the invention provides a syringe cartridge for use with a syringe applicator, wherein the syringe cartridge has a body adapted to contain a fluid for dispensing, a dispensing end having a needle adapted to allow the fluid to be expelled from the body, and a non-dispensing end, whereby in use pressure applied to the cartridge by a syringe will drive the fluid from the needle of the syringe cartridge.

Preferably there are a plurality of syringe cartridges held in a spaced apart configuration on a feeding strip.

Preferably each cartridge has a body and a floating piston adapted to be moved by the plunger of the applicator.

Alternatively each cartridge may be in the form of a squeezable pouch.

In a further aspect the invention provides a syringe cartridge strip for use with a syringe cartridge applicator, wherein the syringe cartridge strip has a base portion adapted to be received by the syringe cartridge applicator, said base portion supporting a plurality of syringe cartridges thereon, each syringe cartridge having a body adapted to contain a fluid for dispensing, a dispensing end adapted to allow the fluid to be expelled from the body, and a non-dispensing end, whereby in use pressure applied to the non-dispensing end of the syringe cartridge by the syringe cartridge applicator will drive the fluid from the dispensing end of the syringe cartridge, and wherein the base portion of the syringe cartridge strip has indexing means to enable automatic indexing of the syringe cartridge strip by the syringe cartridge applicator.

Preferably, the non-dispensing end of each syringe cartridge is closed by a movable piston having an outer surface adapted to be engaged by a plunger assembly of the syringe cartridge applicator.

In another aspect the invention broadly consists in a syringe device having housing and a receptor for one or more pre-loaded syringe cartridges, comprising:

(a) An applicator trigger moveable in a first direction from an extended position to a retracted position;

(b) A plunger assembly interfaced with the applicator trigger, and located in close proximity to the receptor, wherein movement of the applicator trigger from the extended position to the retracted position results in the plunger assembly driving the fluid from the syringe cartridge; and (c) the receptor comprising a syringe cartridge holding assembly, the syringe cartridge holding assembly adapted to removably receive the syringe cartridge in a dispensing position, wherein the syringe cartridge holding assembly is adapted to hold the syringe cartridge in the dispensing position such that a longitudinal axis of the syringe cartridge is inclined at a predetermined angle relative to the first direction, the predetermined angle being greater than about 45 degrees and less than about 135 degrees.

Preferably the predetermined angle is greater than about 60 degrees and less than about 120 degrees.

Alternatively the predetermined angle is greater than about 75 degrees and less than about 105 degrees.

Alternatively the longitudinal axis of the syringe cartridge is oriented substantially perpendicular to the first direction.

Preferably the device further includes a syringe cartridge locking assembly, the syringe cartridge locking assembly including a syringe cartridge release moveable between a locking position wherein the syringe cartridge release impedes release of the syringe cartridge from the and a release position, in which the syringe cartridge release does not impede release of the syringe cartridge from the device, wherein the syringe cartridge locking assembly impedes movement of the syringe cartridge release from the locking position to the release position until the syringe cartridge is at least substantially fully dispensed.

Preferably the syringe cartridge dispensing device further includes a biasing assembly for biasing the syringe cartridge to an ejected condition, wherein the biasing assembly is adapted to automatically eject the syringe cartridge once the syringe cartridge release is transitioned from the locking position to the release position.

Preferably the plunger assembly includes a plunger interfaced with the applicator trigger such that when the applicator trigger is transitioned from the extended position to the retracted position a distal end of the plunger is adapted to enter the syringe cartridge and engage a follower disposed in the syringe cartridge to move the follower within the syringe cartridge to drive the fluid from the syringe cartridge, wherein the distal end of the plunger does not sealingly engage the syringe cartridge.

Alternatively the plunger assembly includes a plunger interfaced with the applicator trigger such that when the applicator trigger is transitioned from the extended position to the retracted position a distal end of the plunger is adapted to contact a surface of the syringe cartridge to drive the fluid from the syringe cartridge, without entering the syringe cartridge.

Preferably the syringe cartridge dispensing device includes a guide assembly for slidingly receiving a syringe cartridge in a loading direction oriented substantially perpendicular to the longitudinal axis of the syringe cartridge.

Preferably the guide assembly includes at least one track for slidingly receiving a portion of a flange of the syringe cartridge.

Preferably the applicator trigger is pivotally coupled to the syringe cartridge dispensing device such that the applicator trigger rotates between the extended position and the retracted position.

Preferably the applicator trigger is adapted to receive at least four fingers of a user's hand during movement of the applicator trigger from the extended position to the retracted position.

Preferably the syringe cartridge dispensing device is adapted to receive and dispense the contents of at least one single syringe cartridge.

Preferably the syringe cartridge is part of a syringe cartridge set that can be fed for individual dispensing after ejection of each syringe cartridge.

In a further aspect the invention broadly consists in a syringe cartridge dispensing device for dispensing a fluid from a syringe cartridge, the device comprising:

(a) an applicator trigger moveable from an extended position to a refracted position;

(b) a plunger assembly interfaced with the applicator trigger, wherein movement of the applicator trigger from the extended position to the retracted position results in the plunger assembly driving the fluid from the syringe cartridge;

(c) a syringe cartridge holding assembly, the syringe cartridge holding assembly adapted to removably receive the syringe cartridge in a dispensing position;

(d) a syringe cartridge locking assembly, the syringe cartridge locking assembly including a syringe cartridge release moveable between a locking position wherein the syringe cartridge release impedes release of the syringe cartridge from the device and a release position, in which the syringe cartridge release does not impede release of the syringe cartridge from the device, wherein the syringe cartridge locking assembly impedes movement of the syringe cartridge release from the locking position to the release position until the applicator trigger is in the retracted position; and (e) a biasing assembly for biasing the syringe cartridge to an ejected condition, wherein the biasing assembly is adapted to automatically eject the syringe cartridge once the syringe cartridge release is transitioned from the locking position to the release position.

Preferably the syringe cartridge holding assembly is adapted to hold the syringe cartridge in the dispensing position such that a longitudinal axis of the syringe cartridge is inclined at a predetermined angle relative to a direction in which the applicator trigger is moved when moved between the extended position and the retracted position, the predetermined angle being greater than about 45 degrees and less than about 135 degrees.

Preferably the predetermined angle is greater than about 60 degrees and less than about 120 degrees.

Alternatively the predetermined angle is greater than about 75 degrees and less than about 105 degrees.

Alternatively the longitudinal axis of the syringe cartridge is oriented substantially perpendicular to the first direction.

Preferably the plunger assembly includes a plunger interfaced with the applicator trigger such that when the applicator trigger is transitioned from the extended position to the retracted position a distal end of the plunger is adapted to enter the syringe cartridge and engage a follower disposed in the syringe cartridge to move the follower within the syringe cartridge to drive the fluid from the syringe cartridge, wherein the distal end of the plunger does not sealingly engage the syringe cartridge.

Alternatively the plunger assembly includes a plunger interfaced with the applicator trigger such that when the applicator trigger is transitioned from the extended position to the retracted position a distal end of the plunger is adapted to contact a surface of the syringe cartridge to drive the fluid from the syringe cartridge, without entering the syringe cartridge.

Preferably the syringe cartridge dispensing device includes a guide assembly for slidingly receiving a syringe cartridge in a loading direction oriented substantially perpendicular to the longitudinal axis of the syringe cartridge.

Preferably the guide assembly includes at least one track for slidingly receiving a portion of a flange of the syringe cartridge.

Preferably the applicator trigger is pivotally coupled to the syringe cartridge dispensing device such that the applicator trigger rotates between the extended position and the retracted position.

Preferably the applicator trigger is adapted to receive at least four fingers of a user's hand during movement of the applicator trigger from the extended position to the retracted position.

In another aspect the invention broadly resides in a syringe cartridge dispensing device for successively dispensing a fluid from a plurality of syringe cartridges on a syringe cartridge strip, the device comprising:
(a) an applicator trigger moveable from an extended position to a refracted position;
(b) a syringe cartridge holding assembly, the syringe cartridge holding assembly adapted to removably receive the syringe cartridge strip and to hold one of the syringe cartridges on the syringe cartridge strip in a dispensing position;
(c) a plunger assembly interfaced with the applicator trigger, wherein movement of the applicator trigger from the extended position to the retracted position results in the plunger assembly driving the fluid from the syringe cartridge that is in the dispensing position; and
(d) a syringe cartridge indexing assembly interfaced with the applicator trigger and the syringe cartridge holding assembly, wherein the indexing assembly is adapted to move the next syringe cartridge on the syringe cartridge strip into the dispensing position after the contents of the preceding syringe cartridge have been dispensed such that subsequent movement of the applicator trigger from the extended position to the retracted position results in the plunger assembly driving the fluid from the next syringe cartridge in the syringe cartridge strip.

Preferably the syringe cartridge holding assembly is adapted to hold the syringe cartridge in the dispensing position such that a longitudinal axis of the syringe cartridge is inclined at a predetermined angle relative to a direction in which the applicator trigger is moved when moved between the extended position and the retracted position, the predetermined angle being greater than about 45 degrees and less than about 135 degrees.

Preferably the predetermined angle is greater than about 60 degrees and less than about 120 degrees.

Alternatively the predetermined angle is greater than about 75 degrees and less than about 105 degrees.

Alternatively the longitudinal axis of the syringe cartridge is oriented substantially perpendicular to the first direction.

Preferably the plunger assembly includes a plunger interfaced with the applicator trigger such that when the applicator trigger is transitioned from the extended position to the retracted position a distal end of the plunger is adapted to enter the syringe cartridge and engage a follower disposed in the syringe cartridge to move the follower within the syringe cartridge to drive the fluid from the syringe cartridge, wherein the distal end of the plunger does not sealingly engage the syringe cartridge.

Alternatively the plunger assembly includes a plunger interfaced with the applicator trigger such that when the applicator trigger is transitioned from the extended position to the retracted position a distal end of the plunger is adapted to contact a surface of the syringe cartridge to drive the fluid from the syringe cartridge, without entering the syringe cartridge.

Preferably the syringe cartridge dispensing device includes a guide assembly for slidingly receiving a syringe cartridge strip in a loading direction oriented substantially perpendicular to the longitudinal axis of the syringe cartridge.

Alternatively the syringe cartridge dispensing device includes a guide assembly for slidingly receiving a syringe cartridge strip in a loading direction oriented substantially around the circumference of the applicator.

Preferably the guide assembly includes at least one track for slidingly receiving a portion of a flange of the syringe cartridge strip.

Preferably the applicator trigger is pivotally coupled to the syringe cartridge dispensing device such that the applicator trigger rotates between the extended position and the retracted position.

Preferably the applicator trigger is adapted to receive at least four fingers of a user's hand during movement of the applicator trigger from the extended position to the retracted position.

In a another aspect the invention broadly resides in a syringe cartridge strip for use with a syringe cartridge dispensing device, wherein the syringe cartridge strip comprises a base portion adapted to connect a plurality of spaced apart syringe cartridges, each syringe cartridge having a body adapted to contain a fluid for dispensing, a dispensing end adapted to allow the fluid to be expelled from the body, and a non-dispensing end adapted to allow a plunger or other mechanism of the syringe cartridge dispensing device to contact or engage therewith to drive the fluid from the syringe cartridge.

Preferably the base portion comprises an indexing means to enable the syringe cartridge strip to be automatically indexed by the syringe cartridge dispensing device in use.

Preferably the indexing means is in the form of an index hole located between each of the spaced apart syringe cartridges.

Alternatively the indexing means is in the form of a pair of opposing recesses located on each edge of the base portion between each of the spaced apart syringe cartridges.

Preferably the dispensing end of each syringe cartridge on the syringe cartridge strip has a protective cap.

Preferably the fluid contained in each syringe cartridge is sealed within the syringe cartridge and each syringe cartridge includes a piercing mechanism which pierces the seal when release of the fluid in the syringe cartridge is required.

Preferably the non-dispensing end of the syringe cartridge includes a follower which in use is adapted to allow the head of the plunger which is sized to slidingly interfit within the syringe cartridge body, to abut and drive the fluid from the dispensing end of the syringe cartridge.

Alternatively the syringe cartridge is adapted such that the plunger or other mechanism contacts a surface of the non-dispensing end of the syringe cartridge to cause the fluid to be driven from the dispensing end of the syringe cartridge.

In a further aspect the invention broadly resides in a syringe cartridge for use with a syringe cartridge dispensing device, wherein the syringe cartridge strip has a body adapted to contain a fluid for dispensing, a dispensing end having a needle adapted to allow the fluid to be expelled from the body, and a non-dispensing end adapted to allow a plunger or other mechanism of the syringe cartridge dispensing device to contact or engage therewith to drive the fluid from the needle of the syringe cartridge, the non-dispensing end having a base portion adapted to be held by the syringe cartridge holding assembly.

Preferably the non-dispensing end is closed by a movable piston having an outer surface adapted to be engaged by the plunger.

More preferably the piston has an inner surface of a shape complementary to the shape of the dispensing end so that substantially all of the fluid within the body of the cartridge can be expelled via the needle.

Preferably, prior to use, the needle is covered with a releasable safety cap.

Although the tip of each cartridge terminates in a needle to allow injection of the fluid into an animal, it is also possible that the construction of the invention may have application to the dispensing of other metered or predetermined volumes of fluid from a dispenser.

Thus in a further aspect the invention broadly consists in a syringe cartridge dispensing device for dispensing a fluid from a cartridge, the cartridge dispensing device comprising:
(a) An applicator trigger moveable in a first direction from an extended position to a retracted position;
(b) A plunger assembly interfaced with the applicator trigger, wherein movement of the applicator trigger from the extended position to the retracted position results in the plunger assembly driving the fluid from the cartridge; and
(c) A cartridge holding assembly, the cartridge holding assembly adapted to removably receive the cartridge in a dispensing position, wherein the cartridge holding assembly is adapted to hold the cartridge in the dispensing position such that a longitudinal axis of the cartridge is inclined at a predetermined angle relative to the first direction, the predetermined angle being greater than about 45 degrees and less than about 135 degrees.

Preferably the predetermined angle is greater than about 60 degrees and less than about 120 degrees.

Alternatively the predetermined angle is greater than about 75 degrees and less than about 105 degrees.

Alternatively the longitudinal axis of the cartridge is oriented substantially perpendicular to the first direction.

Preferably the device further includes a cartridge locking assembly, the cartridge locking assembly including a cartridge release moveable between a locking position wherein the cartridge release impedes release of the cartridge from the device and a release position, in which the cartridge release does not impede release of the cartridge from the device, wherein the cartridge locking assembly impedes movement of the cartridge release from the locking position to the release position until the cartridge is at least substantially fully dispensed.

Preferably the cartridge dispensing device further includes a biasing assembly for biasing the cartridge to an ejected condition, wherein the biasing assembly is adapted to automatically eject the cartridge once the cartridge release is transitioned from the locking position to the release position.

Preferably the plunger assembly includes a plunger interfaced with the applicator trigger such that when the applicator trigger is transitioned from the extended position to the retracted position a distal end of the plunger is adapted to enter the cartridge and engage a follower disposed in the cartridge to move the follower within the cartridge to drive the fluid from the cartridge, wherein the distal end of the plunger does not sealingly engage the cartridge.

Alternatively the plunger assembly includes a plunger interfaced with the applicator trigger such that when the applicator trigger is transitioned from the extended position to the retracted position a distal end of the plunger is adapted to contact a surface of the cartridge to drive the fluid from the cartridge, without entering the cartridge.

Preferably the cartridge dispensing device includes a guide assembly for slidingly receiving a cartridge in a loading direction oriented substantially perpendicular to the longitudinal axis of the cartridge.

Preferably the guide assembly includes at least one track for slidingly receiving a portion of a flange of the cartridge.

Preferably the applicator trigger is pivotally coupled to the cartridge dispensing device such that the applicator trigger rotates between the extended position and the retracted position.

Preferably the applicator trigger is adapted to receive at least four fingers of a user's hand during movement of the applicator trigger from the extended position to the retracted position.

Preferably the cartridge dispensing device is adapted to receive and dispense the contents of at least one single cartridge.

Preferably the cartridge is part of a cartridge set that can be fed for individual dispensing after ejection of each cartridge.

In a still further aspect the invention broadly consists in a cartridge dispensing device for dispensing a fluid from a cartridge, the device comprising:
(a) an applicator trigger moveable from an extended position to a retracted position;
(b) a plunger assembly interfaced with the applicator trigger, wherein movement of the applicator trigger from the extended position to the retracted position results in the plunger assembly driving the fluid from the cartridge;
(c) a cartridge holding assembly, the cartridge holding assembly adapted to removably receive the cartridge in a dispensing position;
(d) a cartridge locking assembly, the cartridge locking assembly including a cartridge release moveable between a locking position wherein the cartridge release impedes release of the cartridge from the device and a release position, in which the cartridge release does not impede release of the cartridge from the device, wherein the cartridge locking assembly impedes movement of the cartridge release from the locking position to the release position until the applicator trigger is in the retracted position; and
(e) a biasing assembly for biasing the cartridge to an ejected condition, wherein the biasing assembly is adapted to automatically eject the cartridge once the cartridge release is transitioned from the locking position to the release position.

Preferably the cartridge holding assembly is adapted to hold the cartridge in the dispensing position such that a longitudinal axis of the cartridge is inclined at a predetermined angle relative to a direction in which the applicator trigger is moved when moved between the extended position and the retracted position, the predetermined angle being greater than about 45 degrees and less than about 135 degrees.

Preferably the predetermined angle is greater than about 60 degrees and less than about 120 degrees.

Alternatively the predetermined angle is greater than about 75 degrees and less than about 105 degrees.

Alternatively the longitudinal axis of the cartridge is oriented substantially perpendicular to the first direction.

Preferably the plunger assembly includes a plunger interfaced with the applicator trigger such that when the applicator trigger is transitioned from the extended position to the retracted position a distal end of the plunger is adapted to enter the cartridge and engage a follower disposed in the cartridge to move the follower within the cartridge to drive the fluid from the cartridge, wherein the distal end of the plunger does not sealingly engage the cartridge.

Alternatively the plunger assembly includes a plunger interfaced with the applicator trigger such that when the applicator trigger is transitioned from the extended position to the retracted position a distal end of the plunger is adapted to contact a surface of the cartridge to drive the fluid from the cartridge, without entering the cartridge.

Preferably the cartridge dispensing device includes a guide assembly for slidingly receiving a cartridge in a loading direction oriented substantially perpendicular to the longitudinal axis of the cartridge.

Preferably the guide assembly includes at least one track for slidingly receiving a portion of a flange of the cartridge.

Preferably the applicator trigger is pivotally coupled to the cartridge dispensing device such that the applicator trigger rotates between the extended position and the refracted position.

Preferably the applicator trigger is adapted to receive at least four fingers of a user's hand during movement of the applicator trigger from the extended position to the retracted position.

In a yet further aspect the invention broadly resides in a cartridge dispensing device for successively dispensing a fluid from a plurality of cartridges on a cartridge strip, the device comprising:
(a) an applicator trigger moveable from an extended position to a refracted position;
(b) a cartridge holding assembly, the cartridge holding assembly adapted to removably receive the cartridge strip and to hold one of the cartridges on the cartridge strip in a dispensing position;
(c) a plunger assembly interfaced with the applicator trigger, wherein movement of the applicator trigger from the extended position to the retracted position results in the plunger assembly driving the fluid from the cartridge that is in the dispensing position; and
(d) a cartridge indexing assembly interfaced with the applicator trigger and the cartridge holding assembly, wherein the indexing assembly is adapted to move the next cartridge on the cartridge strip into the dispensing position after the contents of the preceding cartridge have been dispensed such that subsequent movement of the applicator trigger from the extended position to the retracted position results in the plunger assembly driving the fluid from the next cartridge in the cartridge strip.

Preferably the cartridge holding assembly is adapted to hold the cartridge in the dispensing position such that a longitudinal axis of the cartridge is inclined at a predetermined angle relative to a direction in which the applicator trigger is moved when moved between the extended position and the retracted position, the predetermined angle being greater than about 45 degrees and less than about 135 degrees.

Preferably the predetermined angle is greater than about 60 degrees and less than about 120 degrees.

Alternatively the predetermined angle is greater than about 75 degrees and less than about 105 degrees.

Alternatively the longitudinal axis of the cartridge is oriented substantially perpendicular to the first direction.

Preferably the plunger assembly includes a plunger interfaced with the applicator trigger such that when the applicator trigger is transitioned from the extended position to the retracted position a distal end of the plunger is adapted to enter the cartridge and engage a follower disposed in the cartridge to move the follower within the cartridge to drive the fluid from the cartridge, wherein the distal end of the plunger does not sealingly engage the cartridge.

Alternatively the plunger assembly includes a plunger interfaced with the applicator trigger such that when the applicator trigger is transitioned from the extended position to the retracted position a distal end of the plunger is adapted to contact a surface of the cartridge to drive the fluid from the cartridge, without entering the cartridge.

Preferably the cartridge dispensing device includes a guide assembly for slidingly receiving a cartridge strip in a loading direction oriented substantially perpendicular to the longitudinal axis of the cartridge.

Alternatively the cartridge dispensing device includes a guide assembly for slidingly receiving a cartridge strip in a loading direction oriented substantially around the circumference of the applicator.

Preferably the guide assembly includes at least one track for slidingly receiving a portion of a flange of the cartridge strip.

Preferably the applicator trigger is pivotally coupled to the cartridge dispensing device such that the applicator trigger rotates between the extended position and the retracted position.

Preferably the applicator trigger is adapted to receive at least four fingers of a user's hand during movement of the applicator trigger from the extended position to the retracted position.

In another aspect the invention broadly resides in a cartridge strip for use with a cartridge dispensing device, wherein the cartridge strip comprises a base portion adapted to connect a plurality of spaced apart cartridges, each cartridge having a body adapted to contain a fluid for dispensing, a dispensing end adapted to allow the fluid to be expelled from the body, and a non-dispensing end adapted to allow a plunger or other mechanism of the cartridge dispensing device to contact or engage therewith to drive the fluid from the cartridge.

Preferably the base portion comprises an indexing means to enable the cartridge strip to be automatically indexed by the cartridge dispensing device in use.

Preferably the indexing means is in the form of an index hole located between each of the spaced apart cartridges.

Alternatively the indexing means is in the form of a pair of opposing recesses located on each edge of the base portion between each of the spaced apart cartridges.

Preferably the dispensing end of each cartridge on the cartridge strip has a protective cap.

Preferably the fluid contained in each cartridge is sealed within the cartridge and each cartridge includes a piercing mechanism which pierces the seal when release of the fluid in the cartridge is required.

Preferably the non-dispensing end of the cartridge includes a follower which in use is adapted to allow the head of the plunger which is sized to slidingly interfit within the cartridge body, to abut and drive the fluid from the dispensing end of the cartridge.

Alternatively the cartridge is adapted such that the plunger or other mechanism contacts a surface of the non-dispensing end of the cartridge to cause the fluid to be driven from the dispensing end of the cartridge.

BRIEF DESCRIPTION OF THE DRAWINGS

The invention will now be described, by way of example only, by reference to the accompanying drawings:

FIG. 1 is a perspective view of a syringe cartridge (with cap removed) for use with a syringe cartridge dispensing device in accordance with a preferred embodiment of the invention.

FIG. 2 is a perspective view of a syringe cartridge dispensing device for dispensing a single syringe cartridge (syringe cartridge not shown).

FIG. 3 is a perspective view of the syringe cartridge dispensing device of FIG. 2 with a syringe cartridge in position.

FIG. 4 is a perspective view of the inner workings of a syringe cartridge dispensing device, in a neutral position just prior to removal of the protective cap over the needle.

FIG. 5 is a perspective view of the inner workings of a syringe cartridge dispensing device, after a dose has been administered.

FIG. 6 is a perspective view of the inner workings of a syringe cartridge dispensing device, with the trigger partially released, and the plunger retracting.

FIG. 7 is a perspective view of the inner workings of a syringe cartridge dispensing device, with the syringe cartridge release mechanism activated.

FIG. 8 is a side view of a second embodiment of a syringe cartridge dispensing device for use with multiple syringe cartridges.

FIG. 9 is a side view of the syringe cartridge dispensing device shown in FIG. 8, with the multiple syringe cartridges loaded in the applicator.

FIG. 10 is a cross-section side view of a syringe cartridge dispensing device in accordance with a preferred embodiment of the invention.

FIG. 10A is a cross-section side view of the preferred syringe cartridges for use with the syringe cartridge dispensing device shown in FIG. 10.

FIG. 11 is a cross-section side view of a syringe cartridge dispensing device with the syringe cartridge strip part loaded.

FIG. 12 is a cross-section side view of a syringe cartridge dispensing device with the syringe cartridge strip loaded to a stop position.

FIG. 15 is a cross-section side view of a syringe cartridge dispensing device showing the plunger fully returned and the syringe cartridge partially indexed.

FIG. 16 is a cross-section side view of a syringe cartridge dispensing device showing the handle fully returned and the syringe cartridge indexed ready for the next dose.

FIG. 17 is a side view of a further embodiment of a syringe cartridge dispensing device.

FIG. 18 is a perspective view of the syringe cartridge dispensing device of FIG. 17.

FIG. 18A is a side view of a syringe cartridge strip for use in the syringe cartridge dispensing device of FIGS. 17 and 18.

FIG. 18B is a perspective view of a further embodiment of a syringe cartridge strip for use in a syringe cartridge dispensing device.

FIG. 18C is a perspective view of a further embodiment of a syringe cartridge strip for use in a syringe cartridge dispensing device.

FIG. 19 is a side view of a further embodiment of a syringe cartridge dispensing device with a variation in the syringe cartridge holding assembly.

FIG. 20 is a perspective view of the syringe cartridge dispensing device of FIG. 19.

FIG. 21 is a side view of a further embodiment of a syringe cartridge dispensing device with a further variation in the syringe cartridge holding assembly.

FIG. 22 is a perspective view of the syringe cartridge dispensing device of FIG. 21.

FIG. 23 is a side view of a further embodiment of a syringe cartridge dispensing device with a further variation in the syringe cartridge holding assembly.

FIG. 24 is a perspective view of the syringe cartridge dispensing device of FIG. 23.

FIG. 27 is a side view of a further embodiment of a syringe cartridge dispensing device with a further variation in the syringe cartridge holding assembly.

FIG. 27A shows a further embodiment of a syringe cartridge strip for use with a syringe cartridge dispensing device.

FIG. 28 is a side view of the embodiment of FIG. 27, but showing ejection of the syringe cartridge strip from the front rather than the rear.

FIGS. 30A to 30N show further embodiments of syringe cartridge strips for use in a multiple syringe cartridge dispensing device.

FIGS. 31A to 31C show a further embodiment of a syringe cartridge strip for use in a syringe cartridge dispensing device.

FIGS. 32A to 32C show a further embodiment of a syringe cartridge strip for use in a syringe cartridge dispensing device.

FIG. 33 is a side view of a further embodiment of a syringe cartridge dispensing device.

FIG. 34 is a perspective view of the syringe cartridge dispensing device of FIG. 33.

FIGS. 35A to 35D show a further embodiment of a syringe cartridge dispensing device.

Figure 13:
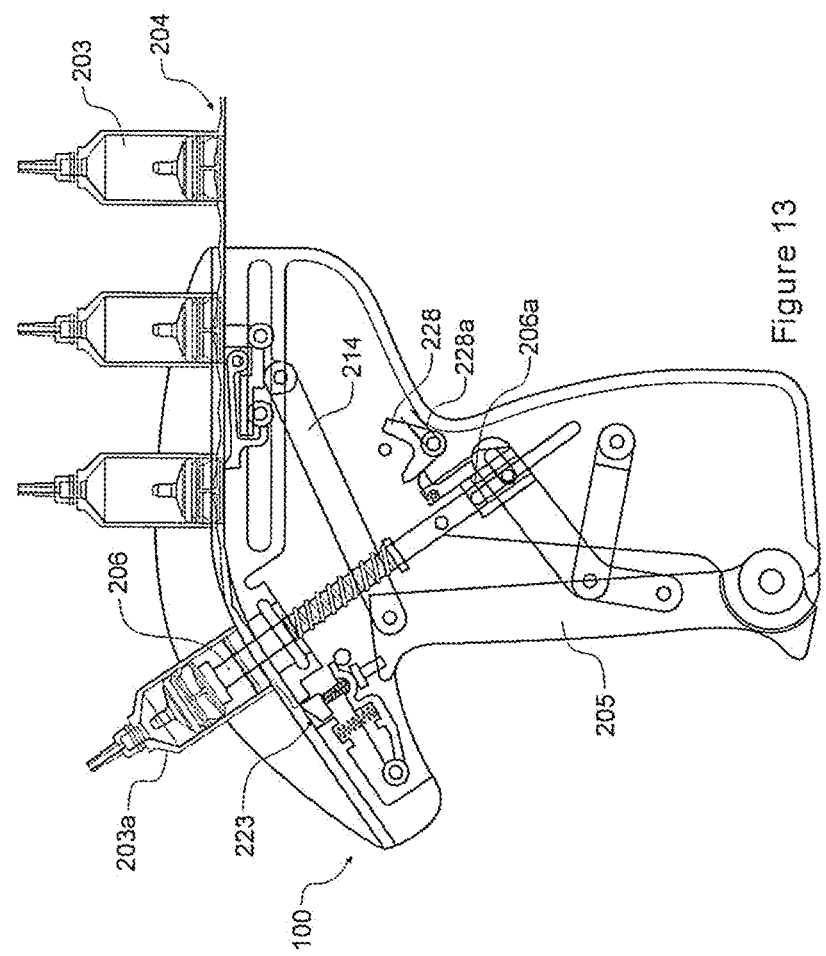
FIG. 13 is a cross-section side view of a syringe cartridge dispensing device showing a dose being partly delivered.

Although the embodiments are illustrated and described particularly for use in intramammary antibiotic applications, it should be noted that this is solely for illustrative purposes only.

The syringe cartridge dispensing devices may be used in any application wherein a fluid is required to be dispensed from a syringe. Further, the term "cartridge" is used in a general sense in this detailed description. Moreover, the term "cartridge" is defined as a container for holding a fluid, a few suitable examples being syringes, magazines, barrels and cases, and wherein fluid includes liquids, gases, and solids having fluid like properties, such as powders, and combinations thereof. There also may be some applications where the device of this invention could be used with cartridges which do not have a needle tip.

DETAILED DESCRIPTION OF PREFERRED EMBODIMENTS

The following description will describe the invention in relation to preferred embodiments of the invention, namely a syringe cartridge dispensing device. The invention is in no way limited to these preferred embodiments as they are purely to exemplify the invention only and possible variations and modifications which would be readily apparent are intended to be included without departing from the scope of the invention.

FIGS. 1-7 show one embodiment of the invention relating to a syringe cartridge dispensing device for dispensing the contents of a single syringe cartridge to provide a single dose of medicament to an animal. FIGS. 8-29 show further embodiments of the invention relating to a syringe cartridge dispensing device for successively dispensing the contents of multiple syringe cartridges to provide multiple doses of a medicament to one or more animals.

Each cartridge, whether stand alone or provided on a carrier strip, has a needle tip. In the case of cartridges for use in intramammary injections of anti-biotics, the needle tips are relatively short as this facilitates handling (in the case of the single cartridges) and also makes it easier to remove the protective caps. However, in some applications longer needles may be required. The drawings show only short needles attached to the dispensing end of each cartridge.

Single Syringe Cartridge Dispensing Device

The syringe cartridge dispensing device (generally indicated at 1 of FIG. 2) is adapted to dispense a fluid from a syringe cartridge 3 (FIG. 1). Syringe cartridge 3 has a body 4 formed with sidewalls and ends adapted to contain the fluid for dispensing, the body having a dispensing end 5 and non-dispensing end 6. Dispensing end 5 is adapted to allow the fluid to be expelled from body 4 via a short needle at its tip, and non-dispensing end 6 is adapted and constructed to allow a plunger to enter and exit therefrom. Device 1 includes an applicator trigger 10 pivotally coupled by pivot means 10a (FIG. 4) to a syringe cartridge holding assembly 11 wherein such a trigger is movable in a first direction 12 as shown in FIG. 2. Trigger 10 is also operatively attached to a plunger assembly 13 as shown in FIGS. 4-7 so that movement of the trigger 10 from an extended position to a retracted position results in the plunger assembly moving through a defined stroke, driving fluid from the syringe cartridge. The trigger 10 is shaped and dimensioned to receive during use at least four fingers of a user's hand during movement of the applicator trigger from the extended position to the retracted position. The ergonomics of the device are important, in particular the angle or relationship of the syringe cartridge and nozzle to the user's hand and wrist and the distribution of the dispensing force over a wider group of muscles in the hand.

In all cases it is preferable that the cartridge body is formed of a transparent or translucent material. Typically the cartridge body would be blow moulded or injection moulded from a transparent plastics material, so that the position of the follower (floating plunger) would be visible. Indeed it is preferable that the follower (described below) is coloured so that its movement down the body of the cartridge can be readily checked. It is preferable that this combination of a coloured follower and a transparent or translucent body enables the operator to quickly check to see that the contents of the cartridge have been fully dispensed through the needle of the syringe.

The syringe cartridge holding assembly 11 is adapted to removably receive and hold the syringe cartridge 3 in a dispensing position in an orientation or inclination at a predetermined angle being defined in relation to a second direction 14 (the longitudinal axis of the syringe cartridge and of the plunger assembly 13) with respect to the first direction 12. The predetermined angle can be for example greater than 45 degrees and less than 135 degrees, between 60 and 120 degrees, between 75 and 105 degrees, or 90 degrees.

The device 1 may also include a syringe cartridge locking assembly 16 which includes a syringe cartridge release means 17 movable between a locking position where the syringe cartridge release means 17 impedes the release of the syringe cartridge 3 from the device 1, and a release position in which the syringe cartridge release means 17 does not impede release of the syringe cartridge from the device 1. The syringe cartridge locking assembly 16 impedes movement of the syringe cartridge release means from the locking position to the release position until the syringe cartridge 3 is at least substantially fully dispensed as shown in FIG. 5.

The plunger assembly 13 includes a slidably mounted floating latch means 19 being operatively attached to a plunger 20. Plunger 20 comprises a shaft 21 operatively joined or connected to a head member 22. Head member 22 is sized to slidingly interfit within the syringe cartridge body to in use allow plunger 20 to move from the non-dispensing end to the dispensing end of syringe cartridge 3. Syringe cartridge 3 has a follower 27 (a "floating piston") being located at the non-dispensing end of the syringe cartridge 3 and in use is adapted to allow the plunger head 20 to abut and push the fluid from the syringe cartridge body. The follower has "O"-ring seals to provide a sterile barrier between the liquid contents of the cartridge and the plunger. The follower is shaped so as to be complementary to the interior of the dispensing end of the cartridge. This enables the follower to be pushed right up to the end of the barrel of the cartridge to expel substantially all of the liquid from within the cartridge. Since the cartridge is a defined size and is filled to a defined amount of liquid, it is possible to ensure that each cartridge delivers a predetermined amount of liquid when used with the cartridge dispensing device of this invention. The syringe cartridge release means 17 includes a body being pivotally coupled to the trigger 10 and to the plunger assembly 13. The syringe cartridge release means 17 includes a body having a lever portion 23.

Trigger 10 includes an arm 24 whereby one end of the arm is fixedly located at one end of the trigger. The distal end of the arm includes a detent means 25 which is slidably and captively located within a track 26 of the floating latch means 19 to in use move upwards when the trigger 10 is moved or rotated, to push the plunger head 22 which in turn pushes the syringe cartridge follower 27 to then slidably move up or down within the syringe cartridge body to push and dispense the fluid contents out of the syringe cartridge 3. Floating latch means 19 comprises a hollow or framed body which slidably captures the plunger shaft 21.

First biasing means (not shown) which can be in the form of a spring is provided with the syringe cartridge release means 17 and is for biasing the release means and syringe cartridge to an injected position and is adapted to automatically eject the syringe cartridge 3 once the syringe cartridge release means 17 is moved from the locking position to the release position. A second biasing means (not shown) which can be in the form of a compression spring acting on the plunger provides a restoring force to the trigger 10 to its rest or starting position as shown in FIG. 2.

Alternatively the cartridges can be inserted by hand and ejected by hand. The shape of the applicator allows the user to push the cartridge into position with his thumb and to push the spent cartridge out using his thumb.

The syringe cartridge includes an overhang portion located at the non dispensing end of the syringe cartridge. The overhang can be in the form of a flange, lip or rim 32 that can be comprised of discrete portions or be in the form of a continuous lip, rim, or flange 32. The syringe cartridge dispensing device 1 may include a guide assembly 33 for slidingly receiving a syringe cartridge 3 in a loading direction oriented substantially perpendicular to the longitudinal axis 14 of the syringe cartridge. Guide assembly 33 includes at least one track (not shown) for slidingly receiving a portion of the flange, lip, or rim of the syringe cartridge 3.

In use, the syringe cartridge dispensing device has a front 37, rear face 38, top 39, and bottom 40 as shown in FIG. 3. The device includes a casing which functions as shown in FIG. 3 as a cover portion 35 to the mechanisms of the device and to the trigger 10 and also as a handle portion 36 to allow the trigger to be moved with respect to the handle portion 36. The handle portion 36 also provides housing for the second biasing means or compression spring to abut against to provide a biasing force for the plunger. Also shown in FIG. 3, the cover portion 35 and a top part of the trigger, form together an aperture having overhanging sections and inner side walls with the track (not shown) of the guide assembly 33 to form the syringe cartridge holding assembly 11 whereby part of the syringe cartridge release means and lever portion 23 is exposed to view whereby a syringe cartridge 3 can be loaded into the track from the front 37 with the syringe cartridge base 6 resting on the lever portion 23 when properly in place having been pushed forward until the syringe cartridge abuts the inner rear face 38 of the cover portion 35.

The syringe cartridge is loaded from the front 37 of the device 1. Overhanging sections each side of the syringe cartridge holding assembly 11 prevent the syringe cartridge from moving vertically. The sidewalls of the syringe cartridge holding assembly 11 prevent the syringe cartridge from moving horizontally or sideways. As the syringe cartridge is loaded, the syringe cartridge release means 17 pivots downwards (out of the way) allowing the syringe cartridge 3 to pass over the top. Once the syringe cartridge 3 has moved past the syringe cartridge release means 17, the syringe cartridge release means 17 then pivots upwards (force provided by the first biasing means or spring acting on the syringe cartridge release means) and prevents the syringe cartridge 3 from moving forward. The back wall of the syringe cartridge holding assembly 11 prevents the syringe cartridge from moving further rearwards. At this stage the syringe cartridge is effectively restrained and supported but is also located/aligned concentrically above the applicator plunger. The ejection spring is located at the rear of the syringe cartridge holding assembly. As the syringe cartridge is inserted into the syringe cartridge holding assembly the syringe cartridge pushes against the ejection spring (not shown) and "loads" the spring. The loaded ejection spring (not shown) provides the force to eject the spent syringe cartridge.

If the syringe cartridge has a protective cap, it is removed. The applicator trigger 10 can then be squeezed to begin its stroke to administer a dose. As the trigger is squeezed the trigger arm 24 moves upwards in an anticlockwise arc. The trigger arm 24 acts against the plunger assembly 13 and moves the plunger assembly 13 vertically upwards. The plunger assembly 13 is guided so that it can only move in a vertical direction. The interface (contact surfaces/connection) between the trigger arm 24 and the plunger assembly 13, allows the trigger arm to move in a rotary motion while the plunger moves only in a vertical motion. The interface on the plunger assembly 13 that the trigger arm 24 acts against is offset to the rear side of the plunger. This allows the pivot means 10a of the trigger 10 to be moved closer to the axis 14 of the plunger assembly 13, while still maintaining the same ratio of movement (ratio of movement between trigger 10 and plunger assembly 13). The axis 14 of the plunger assembly 13 is important to the ergonomics of the syringe cartridge dispensing device as the angle of the plunger assembly 13 determines the angle of the syringe cartridge 3. Another useful feature is the distance from the front of the trigger to the rear of the handle—all users of the applicator should be able to comfortably reach the trigger with their fingers without having to stretch their hand. By moving the pivot point of the trigger closer to the plunger the trigger can be kept closer to the handle and the whole unit can be kept much more compact.

As the plunger assembly 13 moves upwards it carries with it the floating latch means 19. Just as the plunger assembly 13 reaches the top of its stroke (and thereby substantially all the fluid has been dispensed from the syringe cartridge), the floating latch means 19 pushes past a flexible catch or lever portion 23 on the syringe cartridge release means 17. As the trigger 10 is released the plunger assembly 13 begins moving downwards, however the floating latch means 19 does not move as it is held by the syringe cartridge release means 17. A large compression spring (not shown) acting on the plunger assembly 13 provides the force to return the trigger arm 24 and the trigger 10 to its rest/starting position.

When the plunger assembly 13 begins to move downwards, it leaves behind the follower 27, as this is now pushed snugly up against the interior of the dispensing end. As noted above, by making the body of the cartridge form a transparent or translucent material such as PET, or other suitable plastics material (or in some cases from glass), the position of the follower will be readily visible to the user, and he can check to see that the contents of the cartridge have been fully dispensed.

As the plunger assembly 13 nears the bottom of its stroke the floating latch means 19 starts to move downwards (pulled by the plunger head 22) and in turn pulls the syringe cartridge release means 17 downwards in a clockwise arc. At this stage the plunger assembly 13 is now fully retracted (at the bottom or at the beginning of its stroke) from the syringe cartridge 3. As the syringe cartridge release means 17 moves below the flange 32 of the syringe cartridge 3, the syringe cartridge 3 is no longer retained from the front and the syringe cartridge 3 is ejected from the syringe cartridge dispensing device with the force provided by the ejection spring (not shown). This release action is shown in FIG. 7.

The syringe cartridge release means 17 continues arching downwards and away from the floating latch means 19 as the plunger assembly 13 reaches the end of its stroke. When there is no longer any engagement between the syringe cartridge release means 17 and the floating latch means 19, the floating latch means falls down past the syringe cartridge release means 17 and the mechanism is reset to begin again with the beginning of actuation by the trigger 10.

If only a partial dose is administered and the trigger is released the device prevents the cartridge from being released until the full dose has been administered. This feature is beneficial when treating animals, as if for example the animal kicks and the user quickly withdraws the applicator part way through the dose.

Multiple Syringe Cartridge Dispensing Device

As shown in FIGS. 8 and 9 there is a syringe cartridge dispensing device 100 for dispensing fluid from one or more syringe cartridges on a syringe cartridge strip 101. The syringe cartridge strip 101 comprises four syringe cartridges 102 formed on or attached to a common flexible base strip 103. Any number of syringe cartridges can be formed on such a strip, however, in this particular embodiment four syringe cartridges have been shown as the applicator is particularly useful for intramammary applications, and cows have four teats, so one set of syringe cartridges can be used to treat the udder of one cow. Each syringe cartridge 102 has a dispensing end 114 and a non dispensing end 115.

Syringe cartridge dispensing device 100 comprises an applicator trigger 104, a handle 116, a plunger assembly 105 and a syringe cartridge holding assembly 106 contained within a housing 107. The applicator can also include an indexing assembly (not shown in FIGS. 8 and 9). Although in its simplest form the strip based version can rely on the user's thumb to move the strip along a track to position one cartridge at a time in the dispensing position. As they are attached to the strip the spent cartridges are pushed out of the way as the full next full cartridge is moved into position.

The applicator trigger 104 is movable in a first direction from an extended position to a retracted position. The plunger assembly 105 is interfaced with the trigger 104 so that movement of the trigger from the extended position to the retracted position results in the plunger assembly driving the fluid from each syringe cartridge. The syringe cartridge holding assembly 106 is adapted to removably receive and hold the syringe cartridge strip 101 and each individual syringe cartridge 102 in a dispensing position. Preferably, a longitudinal axis of the syringe cartridge is inclined at a predetermined angle relative to the first direction, the predetermined angle being between about 5-90 degrees, and preferably less than about 45 degrees. Alternatively, the longitudinal axis of the syringe cartridge may be disposed substantially parallel to the first direction as shown in FIGS. 33-35.

The syringe cartridge holding assembly 106 includes a slotted or aperture support member for supporting the strip 103 of the syringe cartridge strip and yet allowing access for the plunger assembly. Plunger assembly 105 includes a plunger having a head portion joined to a shaft portion which is housed in a tubular support, and biasing means.

The applicator trigger 104 is rotatably connected to the handle 116. The trigger 104 is also pivotally coupled to a lever arm assembly, which comprises lever arms 111 and 112. One end of lever arm 112 is pivotally coupled to a lower portion of the trigger 104 and the other end of lever arm 111 is pivotally coupled to a lower end of the plunger shaft within the handle 116. The handle 116 is of a similar size as the handle of the single syringe cartridge dispensing device which is adapted to allow a hand to grip it and in turn allow the fingers to be able to comfortably grip and move the trigger.

The other end of the trigger is slidably mounted in a curved track to allow the trigger to be rotated about the lower pivot when being activated by a user. As shown in FIG. 9, the lever arm 111 connected to the lower end of the plunger shaft is rotatably supported by roller means 113 so that in use when the trigger is activated by a user, lever arms 111 and 112 rotate and pivot about a pivot point between them while lever arm 111 moves over roller 113 to push the plunger upwards and cause the expulsion of the fluid contents from the syringe cartridge.

FIGS. 10 and 10A show a syringe cartridge dispensing device (generally indicated at 200) which is adapted and constructed to allow for dispensing of at least one dose of medicament from a single syringe cartridge 203. The single syringe cartridge 203 can be combined with or removably attached to at least one other syringe cartridge 203 to form a syringe cartridge strip 204, each syringe cartridge having a dispensable product therein. Device 200 can be similarly constructed to the device 1 as shown in FIGS. 1-6 whereby there includes an applicator trigger 205 rotatably attached to a plunger assembly 206. Plunger 206 is slidably attached to a handle 207 which together with the applicator trigger 205 forms a housing having an upper end 208 and lower end 209. Trigger 205 in use is located at the front 210 of the applicator and the handle 207 is located at the rear 211.

Trigger 205 is pivotally connected to the handle 207 at pivot 212 at its lower end and the upper end of the trigger is pivotally connected to an indexing assembly. The indexing assembly includes an index link 214; an index carriage 216, an index pawl 220, and an index stop 223. The index link 214 is a lever or rod or elongate strip which is pivotally connected to the trigger 205 at one end and to the index carriage 216 at the other end. The index carriage 216 is slidably located in a track 217 by rollers 218 and 219 located at each end. An index pawl 220 having an index pawl stop face 221 is attached to an upper face of the index carriage 216 to in use roll in a plane parallel to the track 217 and be stopped when moved towards the front 210 of the applicator. A stop cam 222 and index stop 223 are provided. Index stop 223 comprises a rod shaped member having a stop end and fixed with a spring in between. Stop cam 222 comprises a member which is rotatably attached to the housing and biasedly movable against the housing to provide an outwardly facing cam surface which allows the upper end of the trigger 205 to cam against when being used.

Stop cam 222 is rotatably connected to handle 207 and is biased in a downwards direction by spring 222a. Stop cam 222 is caused to rotate by the action of trigger 205 bearing upon the lower cam face. A stop pin 222b prevents excess rotation of stop cam 222. Index stop 223 comprises a member capable of sliding in an axis parallel to plunger 206, a stop end 223a and an abutment 223b. A spring 223c is provided between stop cam 222 and index stop 223 to bias stop end 223a into the stop position (index stop extends beyond track). In the rest position, trigger 205 bears on stop cam 222 pushing it upwards, which causes index stop 223 to be raised into the index stop position, which provides a stop face against which the syringe cartridge strip 204 abuts during the initial loading of the syringe cartridge strip 204.

During operation, trigger 205 is rotated to the retracted position, stop cam 222 is clear of the cam face 205a of trigger 205 and rotates downwards until stop cam 222 abuts stop pin 222b. This action causes index stop 223 to be retracted (index stop retracted ready for index of syringe cartridge strip 204). Following dispensing of the syringe cartridge contents, trigger 205 is allowed to rotate to the extended position, causing syringe cartridge strip 204 to be indexed forward under the action of index pawl 220 via index link 214. When trigger 205 is near its fully extended position, cam face 205a causes stop cam 222 to rotate upwards which in turn causes upward bias to be applied to index stop 223. Index stop end 223a cannot rise fully until index hole 240 of syringe cartridge strip 204 is immediately above it, whereupon index stop 223 rises to the index stop position.

Plunger 206 has a head portion 224 at the upper end and a return spring 225 being located and abutting the underneath of the head portion 224. Operatively connected to the plunger is a guide block 226 at the lower end of the plunger, a plunger release lever 227, and a plunger release pawl 228. Plunger release pawl 228 comprises an L-shaped centrally rotating member operable by way of a return spring 228A. Lever 227 comprises a Z-shaped member whereby a central portion has hooks at each end adapted and sized to engage with a portion of the release pawl 228 when in use. Also attached to the plunger assembly is a boomerang shaped transfer link 229 which is rotatably attached at its other end to the lower end of the applicator trigger 205.

FIG. 10A shows an example of a syringe cartridge strip 204 whereby syringe cartridges 203 are joined at the non-dispensing end by a joining support strip 235 which is frangible or severable between each of the syringe cartridges on the strip. The syringe cartridge strip 204 has a front end 236 and a rear end 237. The support strip 235 has an index hole 240 located between each syringe cartridge 203 on the syringe cartridge strip 204, in order to allow indexing of the syringe cartridges when the syringe cartridge strip is in use with a syringe cartridge dispensing device.

As shown in FIG. 11, a syringe cartridge strip 204 is inserted or loaded into the syringe cartridge holding assembly 238 located at the upper rear of the applicator, until the front end of the strip 236 meets or is stopped by index stop 223. When the syringe cartridge strip is loaded into the syringe cartridge holding assembly, the non-dispensing end of the first syringe cartridge travels over the index pawl 220 and depresses it. After the first syringe cartridge travels over the index pawl 220, the index pawl 220 then rotates upwards to engage the syringe cartridge strip 235 by way of index hole 240 to keep the syringe cartridge firmly in place, as shown in FIG. 12.

To use the syringe cartridge dispensing device, the applicator trigger 205 is pressed towards the handle 207. FIG. 13 shows the device in use with the trigger partially depressed and the dose partly delivered. The trigger 205 is rotatably connected to the handle 207 by a pivot 212 and the trigger 205 is operatively connected to the plunger assembly 206 by the transfer link 229 and the rear link 230 such that when the trigger is activated it causes the plunger 206 to move upwardly at an angle relative to the handle 207 such that it is coincident with the single syringe cartridge about to be dispensed, such that the plunger head 224 operates to push and expel the syringe cartridge contents from the syringe cartridge. The transfer link 229 has rotated with translated upward motion of guide block 226 together with plunger release lever 227 and via abutment face 206a causing plunger 206 to rise. As guide block 226 and release lever 227 and plunger 206 rises, plunger release pawl 228 is rotatably displaced against the bias of plunger release pawl return spring 228a.

FIG. 13 also shows that the cartridge body and at least the dispensing in thereof protrudes slightly from the housing. This enables the user to see the movement of the follower 27 as it moves towards the end of its stroke into contact with the interior of the dispensing end of the cartridge body. Thus the positioning of the cartridge and the transparent or translucent nature of the cartridge body provides a visible check on the operation of the device.

Also, as the trigger 205 is activated, the upper end of the trigger 205 cams against the lower cam surface of the stop cam 222 so that the stop cam 222 drops under action of the spring, allowing the stop cam 222 to spring downward to lower or pull down the index stop 223. Also, as shown in FIG. 13, the index link 214 moves to the right or to the rear of the device causing the index carriage 216 to roll with it, thereby depressing or toggling the index pawl 220.

Figure 14:
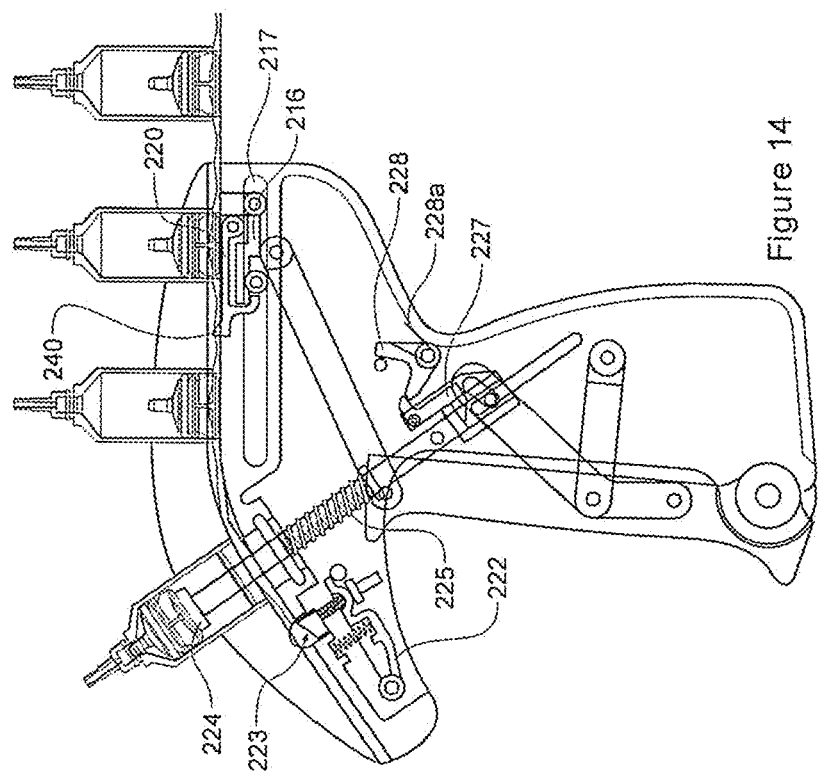
FIG. 14 is a cross-section side view of a syringe cartridge dispensing device showing a full dose delivered.

FIG. 14 shows the syringe cartridge dispensing device when the full dose has been delivered. The plunger head 224 is depressed into the syringe cartridge as far as it can travel and plunger release lever 227 clears the end of plunger release pawl 228 such that plunger release pawl 228 rotates counter clockwise under the action of return spring 228a. Also, the index carriage 216 has now reached the end of the carriage track 217 whereby index pawl 220 engages the syringe cartridge strip in the index hole 240 between the second and third syringe cartridges.

FIGS. 15 and 16 show the workings of the syringe cartridge dispensing device after a dose has been administered, and the trigger 205 has been released. As shown in FIG. 15, when the trigger 205 returns this causes the plunger 206 to retract fully while the syringe cartridge strip 235 glides over the index stop 223 as the index stop 223 is being pulled downwards by stop cam 222. Lever 227 releases plunger 206 before the syringe cartridge is indexed such that the plunger 206 is fully retracted from syringe cartridge strip 235 and the index carriage 216 is dragged forward via index link 214 and trigger 205, under the action of handle return spring. Index pawl 220 pulls syringe cartridge strip 235 forward towards the trigger 205, such that the next syringe cartridge is placed in a dispensing position.

FIG. 16 shows the trigger 205 back in the start position with the first syringe cartridge now empty of its contents, having been administered. The first syringe cartridge is now ready to be cut or ejected from the syringe cartridge dispensing device or will simply be moved forward until all syringe cartridges are dispensed or empty and the entire strip of syringe cartridges is removed or ejected from the device. The plunger assembly 206 is now in line with the second syringe cartridge thereby ready to dispense its contents when the trigger 205 is depressed again. Plunger release lever 227 re-engages the plunger 206, the index carriage 216 has been pulled to the left or front end of the track 217, and the stop of the index pawl 220 has engaged the syringe cartridge strip 235 between the second and third syringe cartridges, but is ready to toggle when required. The release of the trigger 205 pushes the index stop cam 223 into a syringe cartridge index hole 240 to provide a stop.

FIGS. 17-29 show some further examples of possible embodiments of a syringe cartridge dispensing device, where the construction of the syringe cartridge holding assembly located on the upper portion of the body of the device is varied. In general, the syringe cartridge holding assembly has a U-shaped portion which is adapted to allow for the insertion of a syringe cartridge strip. The U-shaped portion has a base and side walls. The base may include grooves or other features depending on the shape or style of the syringe cartridge strip being used in the device. In general, the U-shaped portion runs the entire length of the upper portion of the device for ease of insertion and ejection of the syringe cartridge strips.

FIGS. 17 and 18 show a syringe cartridge dispensing device (generally indicated at 300) including an upper portion 302, a lower portion 303, a rear portion 304, and a front portion 306. The upper portion 302 of the device includes a syringe cartridge holding assembly in the form of a U-shaped portion (generally indicated at 310). The syringe cartridge holding assembly 310 has a base 309 and side walls 308 forming a track or ramp which accommodates the syringe cartridge strip in use. Side walls 308 may have a window 311. At the base of each side wall 308, there is a receiving portion 315, which is sized and shaped to accommodate the base of a syringe cartridge strip to be used in the device. The syringe cartridge dispensing device 300 has an applicator trigger 319 and a rear handle 320. As described above, the applicator trigger 319 is rotatably and operatively connected to the rear handle 320 and to the internal plunger assembly (not shown), to enable the individual syringe cartridges of the syringe cartridge strip to be administered successively as required. The syringe cartridges are inserted into the device at the rear portion 304 and during use the syringe cartridges move towards the front portion 306 (by way of operation of the indexing assembly) as each of their contents are dispensed. The spent syringe cartridges will droop over the front portion of the device until the syringe cartridge strip is removed or ejected from the device.

The syringe cartridge holding assembly 310 of the device may include a mechanism which is adapted to remove a protective cap from the syringe cartridge before the contents are dispensed. For example, in FIGS. 17 and 18, each of the syringe cartridges has a protective cap which is removed by way of a squeeze mechanism. Accordingly, the syringe cartridge holding assembly 310 of the device may include a mechanism on each of the side walls such as opposing notches or the like which will act to squeeze the top of the syringe cartridge when it is in the correct dispensing position to automatically remove the protective cap from the syringe cartridge prior to its contents being dispensed.

FIGS. 18A-18C show some examples of syringe cartridge strips (generally indicated at 305) that may be used in the syringe cartridge dispensing devices. In general, the syringe cartridge strip comprises a base portion adapted to connect a plurality of spaced apart syringe cartridges, each syringe cartridge having a body adapted to contain a fluid for dispensing, a dispensing end adapted to allow the fluid to be expelled from the body, and a non-dispensing end adapted to allow a plunger of the syringe cartridge dispensing device to engage therewith to expel the fluid from the syringe cartridge. The syringe cartridge strips 305 can vary in shape and construction depending on the shape and construction of the syringe cartridge holding assembly 310 of the device and the type of indexing assembly used by the device to move the syringe cartridges through the device. For example, FIG. 18A shows a syringe cartridge strip 305 having concertina shaped links 328 between each individual syringe cartridge.

If the syringe cartridge dispensing device is adapted for automatic indexing of the syringe cartridges, then the base portion of the syringe cartridge strip preferably comprises an indexing means. FIG. 18B shows a syringe cartridge strip 305 having a base portion 325 with indexing means in the form of index holes 326 located between each of the spaced apart syringe cartridges to accommodate the index pawl of the syringe cartridge dispensing device when it engages with the syringe cartridge strip in use. FIG. 18C shows a syringe cartridge strip 305 having a base portion 325 having indexing means in the form of a pair of opposing recesses 327 located on each edge of the base portion between each of the spaced apart syringe cartridges to accommodate the index pawl of the syringe cartridge dispensing device when it engages with the syringe cartridge strip in use.

FIGS. 19 and 20 show another example of a syringe cartridge dispensing device which is similar to the embodiment of FIGS. 17 and 18, however the side walls are cut out 353 in order to improve visibility and finger access to the syringe cartridge holding assembly of the device and the syringe cartridge strips when loaded therein. The cut out side walls 353 may have rails 355 made of stainless steel or other material which may be adapted to remove a protective cap from a syringe cartridge before the contents are dispensed.

FIGS. 21 and 22 show a further example of a syringe cartridge dispensing device. In this embodiment the syringe cartridge holding assembly 363 does not have side walls 361 all along its length. The side walls at the front portion of the device 362 are cut out leaving only the receiving mechanism 360 for receiving the base of the syringe cartridge strip in use. The arrows show the general direction of movement of the syringe cartridge strip during operation of the device. The syringe cartridge strip is loaded from the rear portion 366 and moves towards the front portion 362. In this embodiment the cut out side walls 361 allow for the manual removal of any protective caps from the syringe cartridges before the syringe cartridges are dispensed.

Figure 26:
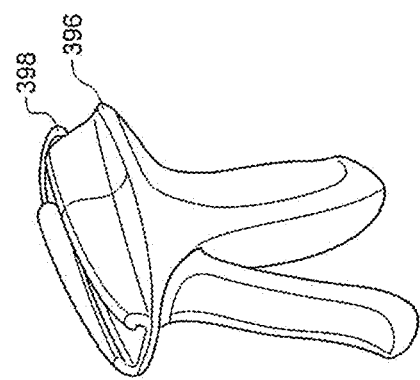
FIG. 26 is a perspective view of the syringe cartridge dispensing device of FIG. 25.
Figure 25:
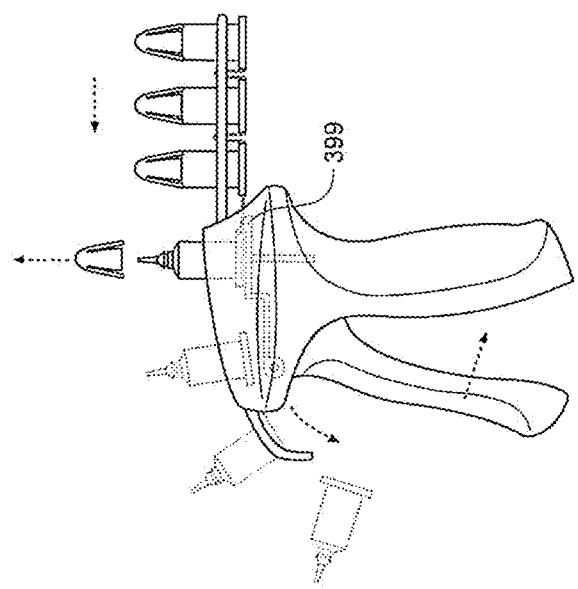
FIG. 25 is a side view of a further embodiment of a syringe cartridge dispensing device with a further variation in the syringe cartridge holding assembly.

FIGS. 23 and 24 show a further example of a syringe cartridge dispensing device. In this embodiment, the syringe cartridge holding assembly includes side walls 371 adapted to accommodate a protruding looped rail 378 which may either be fixed or slidable within the side walls so it can be pushed manually to enable indexing of the syringe cartridges 381. This embodiment allows the syringe cartridge strip to be loaded from the rear 376 and moved towards the front 372 in use, with any protective caps 380 on the syringe cartridges being removed manually. The device may include a cutting means 383 such as a blade for example, in the form of a detent which can be independent or linked to the applicator trigger to cut or sever each syringe cartridge as it is spent. FIGS. 25 and 26 show an example of a syringe cartridge dispensing device very similar to FIGS. 23 and 24, except the looped rail is only looped at one end 398 and only protrudes from the rear 396 of the device, not the front. The rail 398 may again be fixed, or slidably attached to the side walls of the syringe cartridge holding assembly of the device. Again, the syringe cartridge dispensing device may include a cutting means 399 such as a blade for example, in the form of a detent which can be independent or linked to the applicator trigger to cut or sever each syringe cartridge as it is spent.

FIG. 27 shows a further variation of a syringe cartridge dispensing device which includes a rail 455 which protrudes from the front rather than the rear and which enables loading of the syringe cartridge strip from the front and ejection from the rear. It may also enable improved visibility and ease of use. FIG. 27A shows an example of a syringe cartridge strip in which the syringe cartridges have fixed spacing links 456.

FIG. 28 shows still a further variation of a syringe cartridge dispensing device, similar to FIG. 27, which illustrates the possibility that the syringe cartridge strip could be loaded from the front 502, and removal or ejection of the spent syringe cartridges could also occur at the front of the device.

Figure 29:
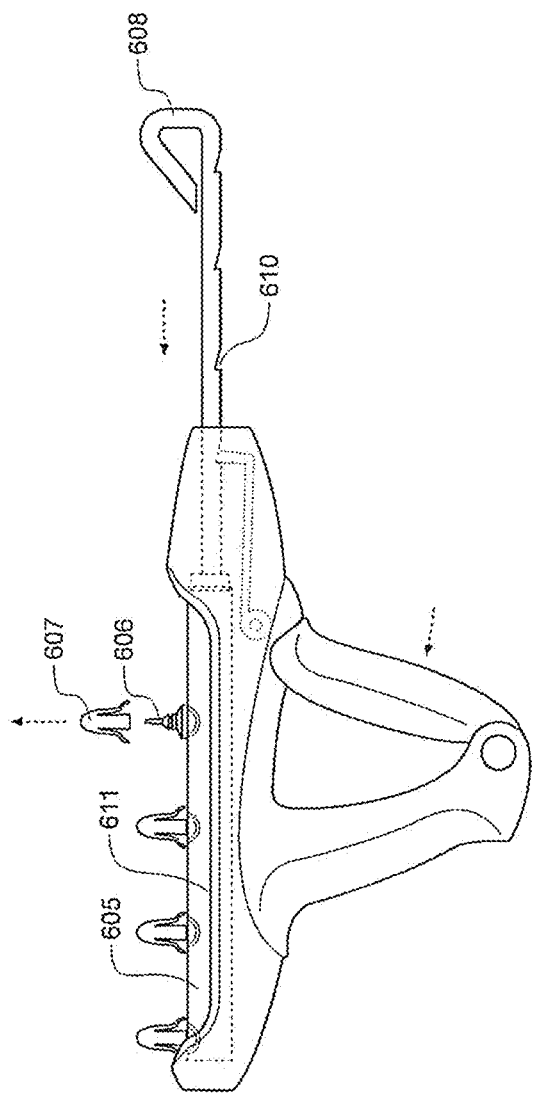
FIG. 29 is a side view of a further embodiment of a syringe cartridge dispensing device and a syringe cartridge strip used therein.

FIG. 29 shows another variation of an embodiment of a syringe cartridge dispensing device which is adapted to receive a different type of syringe cartridge strip. The syringe cartridge strip 605 in this example is in the form of a single cylindrical container having multiple nozzles 606 with individual protective caps 607. The indexing assembly is linked to the syringe cartridge strip 605 which has an indexing means 608 attached to or forming part of the strip 605 and which has notches or recesses 610 therein for engaging the index pawl of the syringe cartridge dispensing device in use. This indexing assembly allows for manual indexing of the syringe cartridges by the user pushing or moving the indexing means 608 as required. The syringe cartridge dispensing device has a syringe cartridge holding assembly with cut out side walls (indicated generally at 611) which enables slidable insertion of the syringe cartridge strip 605 and manual removal of any protective caps.

As would be appreciated by a person skilled in the art, any of the embodiments of the syringe cartridge dispensing device as described herein could be adapted to enable loading and removal or ejection of the syringe cartridge strip in any direction. For example, the device may be adapted to enable loading of the syringe cartridge strip from the front with movement of the syringe cartridge to the rear in use and subsequent removal or ejection of the spent syringe cartridges from the rear. Similarly, the syringe cartridge strips may be loaded and then removed or ejected from the same part of the applicator, for example, loaded and ejected from the front, or loaded and ejected from the rear.

FIGS. 30A to 30N show an embodiment of a syringe cartridge strip, in which the contents of the syringe cartridges are sealed within the syringe cartridge so that the syringe cartridges can be stored for long periods of time without use if necessary. As shown in FIG. 30A, the syringe cartridges have a dispensing end 701 and a base portion 703 which forms the strip attaching all of the syringe cartridges together. Preferably this strip is formed of PET laminate, and both the strip and the body 702 of each cartridge is formed of the same material. Typically each of the cartridges can be blow moulded from the PET of the strip material and the delivery tip comprising the needle attached to the end thereof. The syringe cartridge also has a barrel 702 which contains the sealed contents of the syringe cartridge. The contents are preferably heat sealed with an aluminium seal. FIG. 30B is a cross-section view of FIG. 30A, showing the inside of the syringe cartridge when the plunger of the syringe cartridge dispensing device has not been activated. The syringe cartridge includes a piercing mechanism 704 which pierces the seal when release of the syringe cartridge contents 705 is required. The syringe cartridge also includes a follower 706 being located at the non-dispensing end of the syringe cartridge which in use is adapted to allow the head of the plunger (not shown) to abut and push the fluid from the syringe cartridge towards the dispensing end 701 of the syringe cartridge. FIG. 30C is a cross-section view showing the inside of the syringe cartridge after the plunger of the syringe cartridge dispensing device has been activated. As the plunger is activated (by operation of the applicator trigger), the head of the plunger 707, which may be sized to slidingly interfit within the syringe cartridge body, pushes the follower 706 which in turn pushes the contents 705 of the syringe cartridge up towards the dispensing end 701 of the syringe cartridge such that the seal reaches the piercing mechanism 704 which pierces the seal and allows release of the contents of the syringe cartridge to the dispensing end of the syringe cartridge and thus to the animal to be treated. A diagram of the self-piercing mechanism and process is shown in FIG. 30N. In this diagram the position at the left is prior to operation of the plunger so that the heat sealed aluminium foil 709 provides a secure seal for the liquid within the cartridge body. The seal is just below the piercing nibs 704. In the middle view, the plunger has pressed the follower up into the body of the cartridge so that the volume of liquid forces the aluminium foil 709 upwardly into contact with the piercing nib 704. The numeral 709A shows that the piercing nibs have just pierced the aluminium foil. In the third view on the right hand side of FIG. 30N the piston has continued to push the follower further up into the body of the cartridge forcing the liquid to break the aluminium foil at the throat of the dispensing end, and numeral 709B refers to the breached state of the aluminium foil so that the liquid can escape up through the dispensing end and out through the needle tip. In FIGS. 30A to 30C the barrel of the syringe cartridge is located or protrudes from a single side of the syringe cartridge strip. However, all or part of the barrel of the syringe cartridge may be located or protrude from the underside of the syringe cartridge strip (FIG. 30E), while the dispensing end of the syringe cartridge protrudes from the other side (FIG. 30D). The operation of the plunger inside the syringe cartridge is the same, as shown in FIGS. 30F and 30G.

FIGS. 30H to 30M show a similar embodiment of the syringe cartridges on the syringe cartridge strip; however the barrel of the syringe cartridges are concertina shaped to assist with the release of the contents of the syringe cartridge. With this embodiment of the syringe cartridge strips it is not necessary for the plunger assembly to be shaped or adapted to enter the syringe cartridge body in order to expel its contents. Rather, the plunger assembly can be adapted to contact or apply force to a surface of the syringe cartridge which results in the packaging material collapsing or being substantially squashed to reduce its internal volume, which in turn causes the contents of the syringe cartridge to be squeezed or forced towards the dispensing end of the syringe cartridge resulting in the expulsion of the contents. FIGS. 30H to 30J show a single-sided embodiment where the barrel 702 of the syringe cartridge is attached to or protrudes from only one side of the strip, whereas FIGS. 30K to 30M show a double-sided embodiment where all or part of the barrel 702 of the syringe cartridge protrudes from the underside of the strip and the dispensing end 701 protrudes from the other side.

FIGS. 31A to 31C also show an embodiment of a syringe cartridge strip in which the contents of each syringe cartridge are sealed in a bellows shaped pouch. FIG. 31A shows one side of the syringe cartridge strip with at least part of the pouch and the dispensing end 710 protruding therefrom, while FIG. 31B shows the underside of the strip with the remainder of the pouch 711 protruding therefrom. FIG. 31C is a cross-section view of the syringe cartridge strip showing the sealed contents of the syringe cartridge 712 and the piercing mechanism 713. When the syringe cartridge dispensing device (not shown) is activated, the plunger assembly will push the pouch in the direction of the arrow causing the piercing mechanism to pierce the seal of the pouch and release its contents. FIGS. 32A to 32C show a similar embodiment of the syringe cartridge strip, with different shaped pouches (elongated and flat rather than bellows shaped). When using these syringe cartridge strips it is not necessary for the plunger assembly to be shaped or adapted to enter the syringe cartridge body in order to expel its contents. Rather, the plunger assembly can be adapted to contact or apply force to a surface of the syringe cartridge which results in the packaging material collapsing or being substantially squashed to reduce its internal volume, which in turn causes the contents of the syringe cartridge to be squeezed or forced towards the dispensing end of the syringe cartridge resulting in the expulsion of the contents.

FIGS. 35A to 35D show another possible embodiment of a syringe cartridge dispensing device, preferably using a syringe cartridge strip with a sealed pouch such as shown in FIGS. 31A to 31C and 32A to 32C. In this embodiment of the syringe cartridge dispensing device, the syringe cartridge holding assembly is located around the circumference of the housing of the device and the syringe cartridge strip is fed around the circumference of the device, rather than through the upper surface of the device. The device may include a protective shroud 725 to prevent cross contamination during use. The protective shroud has an aperture 726 from which the dispensing end 727 of the syringe cartridge protrudes when the dose is being administered. FIG. 35C shows how the applicator trigger 729 is operatively connected to the plunger assembly 730 which includes a compression pad 731 at the end thereof, which through operation of a graduated compression force ensures that all of the contents of the syringe cartridge are expelled when the dose is administered (see FIG. 35D). The compression pad 731 does not have to enter each syringe cartridge in order to expel the contents, but rather is adapted to contact or apply force to a surface of the syringe cartridge which results in the packaging material collapsing or being substantially squashed to reduce its internal volume, which in turn causes the contents of the syringe cartridge to be squeezed or forced towards the dispensing end of the syringe cartridge resulting in the expulsion of the contents.

FIGS. 33 and 34 show a further example of a syringe cartridge dispensing device which could be used with any of the syringe cartridge strips described herein. The device has an indexing assembly in the form of a cog 715 which is operatively connected to the plunger assembly 716 and the applicator trigger 717 and is adapted to advance the syringe cartridge strip so the syringe cartridges are loaded in the correct position for successive dosing. The syringe cartridge strip is inserted from the rear 718 of the device and the spent syringe cartridges may either be ejected or removed from the front 719 of the device or could be captured inside the device after use. The rear handle 720 of the device may be attached to a pivot point 721 which allows for the angle of the device to be adjusted during dosing. FIG. 34 shows the upper portion of the device where the syringe cartridge holding assembly 722 is located for receiving the syringe cartridge strip in use. The syringe cartridge holding assembly may be covered with a protective shroud 723 to avoid any potential contamination of the syringe cartridges in use. The protective shroud 723 has an aperture 724 from which the dispensing end of the syringe cartridge protrudes in order to dose the animal.

In general, use of the multiple syringe cartridge dispensing device involves the following steps:

manually loading a syringe cartridge strip into the syringe cartridge holding assembly of the device until the index stop is activated and the first syringe cartridge is in the dispensing position;

depressing the applicator trigger causing activation of the plunger assembly (thereby causing the contents of the first syringe cartridge to be dispensed) while at the same time causing the indexing assembly to begin the process of positioning the next syringe cartridge on the syringe cartridge strip into the dispensing position;

releasing the applicator trigger whereby the plunger assembly pushes back the applicator trigger which in turn results in the indexing assembly moving the syringe cartridge strip forward until the index stop is activated and the next syringe cartridge is in the dispensing position;

Once all of the syringe cartridges on the syringe cartridge strip have been dispensed, the spent strip of syringe cartridges may be removed manually from the device or may simply fall out of the device.

As would be appreciated by a person skilled in the art, many other variations in the construction of the syringe cartridge dispensing device and the syringe cartridge strips may be possible, and the embodiments described herein are examples only.

Advantages

The illustrated embodiments of the syringe cartridge dispensing device provide one or more of the following advantages:

a) The syringe cartridge is held in an improved orientation to facilitate the dispensing of the contents of the syringe cartridge;
b) The applicator trigger is adapted to receive a plurality of fingers to ease the hand strain and fatigue during use by spreading the dispensing force over a wider group of muscles in the hand;
c) The syringe cartridge is prevented from premature release;
d) The syringe cartridge is automatically ejected or moved on, once the contents of the syringe cartridge are fully dispensed;
e) The device can be used with syringe cartridges not having plungers reducing the cost of the syringe cartridges;
f) Due to the syringe cartridges not needing to have separate plunger elements, waste is substantially reduced as this part of a syringe is no longer required. Moreover, if a multiple syringe cartridge dispensing device is used, only syringe cartridge strips are required, rather than multiple syringes, which eliminates a significant amount of waste;
g) The angle of the syringe cartridge when loaded in the syringe cartridge dispensing device is set so that minimal or no twisting of the wrist is required when aligning the nozzle of the syringe cartridge with an animals' teat;
h) The applicator trigger communicates with the plunger via a direct mechanical linkage; therefore the user receives force "feedback" (feel) when administering a dose. Feedback allows the user to monitor and control the administering of each dose;
i) The syringe cartridge dispensing device is quick and simple to load with a single syringe cartridge or a strip of multiple syringe cartridges;
j) The syringe cartridge dispensing device provides a positive indication that the dose contained in the syringe cartridge has been fully administered;
k) The syringe cartridge dispensing device and the syringe cartridges are compact so are able to be easily manoeuvred in the limited space under an animal's udder;
l) The syringe cartridge dispensing device is specifically designed to minimise the risk of contamination;
m) The syringe cartridge strips are designed to ensure a sufficient spacing between nozzles so that the risk of contamination is minimised.

Variations

Throughout the description of this specification, the word "comprise" and variations of that word such as "comprising" and "comprises", are not intended to exclude other additives, components, integers or steps.

It will of course be realised that while the foregoing has been given by way of illustrative example of this invention, all such and other modifications and variations thereto as would be apparent to persons skilled in the art are deemed to fall within the broad scope and ambit of this invention as set forth in the following claims.

What is claimed is:

1. A syringe cartridge applicator for dispensing a fluid from a syringe cartridge, the syringe cartridge applicator comprising:

an applicator trigger, a syringe cartridge holding assembly, and a plunger assembly;
wherein the applicator trigger is pivotally coupled by a pivot means to the syringe cartridge holding assembly, and the applicator trigger is moveable in a first direction from an extended position to a retracted position;
wherein the applicator trigger is operably attached to the plunger assembly so that movement of the applicator trigger from the extended position to the retracted position results in the plunger assembly driving the fluid from the syringe cartridge;
wherein the syringe cartridge holding assembly is adapted to removably receive the syringe cartridge, and to hold the syringe cartridge in a dispensing position such that a longitudinal axis of the syringe cartridge is inclined at a predetermined angle relative to the first direction; wherein the predetermined angle is greater than about 75 degrees and less than about 105 degrees;
wherein when a syringe cartridge is in the dispensing position, the predetermined angle is substantially a right angle; and
wherein the syringe cartridge applicator includes a guide assembly for slidingly receiving a syringe cartridge in a loading direction oriented substantially parallel to the first direction.

2. The syringe cartridge applicator of claim 1, wherein the guide assembly includes at least one track for slidingly receiving a portion of a flange of the syringe cartridge.

3. The syringe cartridge applicator of claim 1, wherein the guide assembly includes at least one track for slidingly receiving a syringe cartridge strip made up of a plurality of individual syringe cartridges supported on a carrier strip.

4. The syringe cartridge applicator of claim 3, wherein the applicator has a syringe cartridge indexing assembly pivotably connected with the applicator trigger and operably connected to the syringe cartridge holding assembly, wherein the syringe cartridge indexing assembly is adapted to move the next syringe cartridge on the syringe cartridge strip into the dispensing position after the fluid from the preceding syringe cartridge has been dispensed such that subsequent movement of the applicator trigger from the extended position to the retracted position results in the plunger assembly driving the fluid from the next syringe cartridge in the syringe cartridge strip.

5. The syringe cartridge applicator of claim 3, wherein the syringe cartridge holding assembly has a base and side walls forming a track or ramp which accommodates the syringe cartridge strip wherein the track or ramp is curved such that the syringe cartridge strip follows a curvilinear path as it moves through the syringe cartridge applicator.

6. The syringe cartridge applicator of claim 3, wherein the applicator includes a cutting means adapted to remove one or more empty syringe cartridges from the syringe cartridge strip after the fluid has been dispensed therefrom.

7. The syringe cartridge applicator of claim 1, wherein the plunger assembly includes a plunger operably connected with the applicator trigger such that when the applicator trigger is transitioned from the extended position to the retracted position a distal end of the plunger is adapted to enter the syringe cartridge and engage a follower disposed in the syringe cartridge to move the follower within the syringe cartridge to drive the fluid from the syringe cartridge, wherein the distal end of the plunger does not sealingly engage the syringe cartridge.

8. A syringe cartridge for use with the syringe cartridge applicator of claim 1, wherein the syringe cartridge has a body adapted to contain a fluid for dispensing, a dispensing end having a needle adapted to allow the fluid to be expelled from the body, and a non-dispensing end, whereby in use pressure applied to the cartridge by a syringe will drive the fluid from the needle of the syringe cartridge.

9. A plurality of syringe cartridges, each cartridge as claimed in claim 8, wherein the cartridges are held in a spaced apart configuration on a feeding-strip.

10. A plurality of syringe cartridges, each cartridge as claimed in claim 9, wherein each cartridge is in the form of a squeezable pouch.

11. The syringe cartridge applicator of claim 1, wherein the plunger assembly includes a plunger operably connect with the applicator trigger such that when the applicator trigger is transitioned from the extended position to the retracted position a distal end of the plunger is adapted to contact a surface of the syringe cartridge to drive the fluid from the syringe cartridge, without entering the syringe cartridge.

12. The syringe cartridge applicator of claim 1, wherein the syringe cartridge holding assembly includes means which are adapted to remove a protective cap from the syringe cartridge before the contents of the syringe cartridge are dispensed; wherein the syringe cartridge holding assembly has a pair of opposing side walls having mechanisms thereon which are adapted to remove the protective cap by contacting one or more protruding shoulders of the protective cap as the syringe cartridge is moved into the dispensing position.

* * * * *